US008394811B2

(12) United States Patent
Samuels et al.

(10) Patent No.: US 8,394,811 B2
(45) Date of Patent: Mar. 12, 2013

(54) HYDRAZIDE COMPOUNDS AS THYROID HORMONE RECEPTOR MODULATORS AND USES THEREOF

(75) Inventors: Herbert H. Samuels, New Rochelle, NY (US); Ruben Abagyan, La Jolla, CA (US); Matthieu Schapira, Toronto (CA); Maxim Totrov, San Diego, CA (US); Bruce M. Raaka, Rockville, MD (US); Stephen R. Wilson, Danville, VA (US); Li Fan, Cambridge, MA (US); Zhiguo Zhou, Winston Salem, NC (US)

(73) Assignees: Molsoft LLC, La Jolla, CA (US); New York University School of Medicine, New York, NY (US)

( * ) Notice: Subject to any disclaimer, the term of this patent is extended or adjusted under 35 U.S.C. 154(b) by 354 days.

(21) Appl. No.: 12/450,922

(22) PCT Filed: Apr. 18, 2008

(86) PCT No.: PCT/US2008/005031
§ 371 (c)(1),
(2), (4) Date: Jul. 2, 2010

(87) PCT Pub. No.: WO2008/130637
PCT Pub. Date: Oct. 30, 2008

(65) Prior Publication Data
US 2010/0286182 A1 Nov. 11, 2010

Related U.S. Application Data

(60) Provisional application No. 60/925,020, filed on Apr. 18, 2007, provisional application No. 60/923,964, filed on Apr. 18, 2007, provisional application No. 60/923,995, filed on Apr. 18, 2007.

(51) Int. Cl.
*A61K 31/438* (2006.01)
*A61K 31/4418* (2006.01)
*A61P 5/16* (2006.01)
*C07D 211/70* (2006.01)
*C07D 471/10* (2006.01)
(52) U.S. Cl. ........... 514/278; 514/357; 546/20; 546/332
(58) Field of Classification Search ........................ None
See application file for complete search history.

(56) References Cited

U.S. PATENT DOCUMENTS
2005/0256144 A1 11/2005 Kath et al.
2006/0229301 A1 10/2006 Nishizawa

OTHER PUBLICATIONS

Vippagunta et al., Crystalline solids, 48 Adv. Drug Delivery Rev. 3-26 (2001).*
Rautio et al., Prodrugs: Design and Clinical Applications, 7 Nat. Rev. Drug Dis., 255-70 (2008).*
Carson-Jurica, M.A., et al., "Steroid Receptor Family: Structure and Functions," Endocrine Reviews, vol. 11, No. 2, 1990, pp. 201-220.
Dees, E.C., et al., "Recent advances in systemic therapy for breast cancer," Curr. Opin. Oncol., vol. 10, pp. 517-522, 1998.
Totrov, M., et al., "In Drug-Receptor thermodynamics: Introduction and Applications," Edited by Raffa, R.B., J. Wiley & Sons, Ltd., 2001, pp. 603-624.
Lazar, M.A., "Throid Hormone Receptors: Multiple forms, Multiple Possiblities," Endocrine Reviews, 14 (2): 1993, pp. 184-193.
Oppenheimer, J.H., et al., "Specific Nuclear Triiodothyronine Binding Sites in Rat Liver and Kidney," J. Clin. Endocrinol. Metab. 35: 1972, pp. 330-333.
Pohlenz, J., et al., "Improved Radioimmunossay for Measurement of Mouse Thyrotropin in Serum; Strain Differences in thyrotropin Concentration and Thyrotroph Sensitivity to Thyroid Hormone," Thyroid, vol. 9, pp. 1265-1271, Nov. 12, 1999.

(Continued)

*Primary Examiner* — Nizal Chandrakumar
*Assistant Examiner* — Timothy R. Rozof
(74) *Attorney, Agent, or Firm* — Klauber & Jackson LLC

(57) ABSTRACT

A method of identification of compounds that modulate thyroid hormone activity, and the use of such compounds and compositions thereof for such purposes are disclosed. The compounds may be selected from the group consisting of:

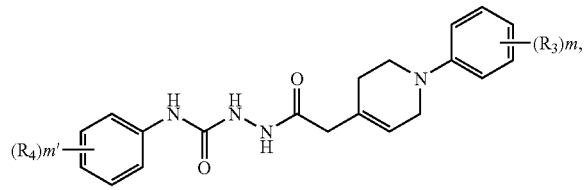

Ia

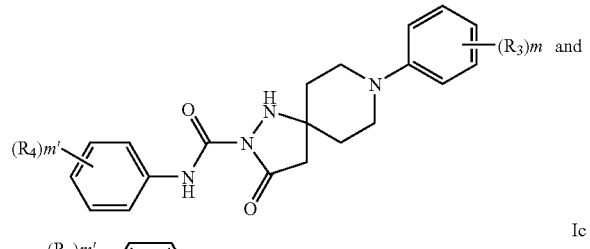

Ib

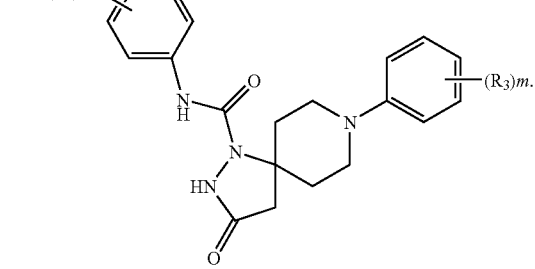

Ic

The compounds may be prepared as pharmaceutical compositions, and may be used for the prevention and treatment of conditions that are causally related to aberrant thyroid hormone activity, such as hyperthyroidism and thyrotoxicosis.

17 Claims, 1 Drawing Sheet

OTHER PUBLICATIONS

Refetoff, S., "Resistance to Thyroid Hormone," Curr. Ther. Endocrinol Metab., vol. 6, 1997, pp. 132-134.

Viswanadhan, V.N., et al., "Knowledge-based approaches in the design and selection of compound libraries for drug discovery," Curr. Opin. Drug Discov. Devel., vol. 5, No. 3, 2002, pp. 400-406.

Taylor, E.C., et al., "A Convenient Synthesis of 1-Aryl-4-piperidones," J.S. Synthesis, vol. 8, 1981, p. 606.

Hu, Y., et al., "Neurosteroid Analogues. 2. Total Synthesis and Electrophysiological Evaluation of Benz[e]indene Analogues of the Anesthetic Steroid Alphaxalone," J. Org. Chem., vol. 60, 1995, pp. 3619-3625.

Wang, G., et al., "Synthetic routs to L-carnitine and L-gamma-amino-beta-hydroxybutyric acid from (S)-3-hydroxybutyrolactone by functional group priority switching," Asymmetry 10 (1999) pp. 1895-1901.

Plenat, F., et al., "Synthesis of New Phosphorus 2,4,6-Imidazolidinetriones," Tetrahedron, vol. 51, No. 35, 1995, pp. 9551-9558.

Mahajan, M.A., et al., "A New Family of Nuclear Receptor Coregulators That Integrate Nuclear Receptor Signaling through CREB-Binding Protein," Molecular and Cellular Biology, Jul. 2000, vol. 20, No. 14, pp. 5048-5063.

Weiss, R.E., et al., "Thyrotropin regulation by thyroid hormone in thyroid hormone receptor beta-deficient mice," Endrocrinology, (1997) vol. 138, pp. 3624-3629.

Abagyan, R., et al., "Biased Probability Monte Carlo Conformational Searches and Electrastatic Calculations for Peptides and Proteins," J. Mol. Biol. (1994), 235, pp. 983-1002.

Abagyan, R., et al., "High-throughoutput docking for lead generation," Current Opinion in Chemical Biology, 5, pp. 375-382, 2001.

Abagyan R,. et al., "Homology Modeling With Internal Coordinate Mechanics: Deformation Zone Mapping and Improvements of Models via Conformational Search," Proteins, Function and Genetics, Suppl., 1:29-37 (1997).

Ajay, W., et al., "Can We Learn to Distinguish between 'Drug-Like' and 'Nondrug-like' Molecules?," J. Med. Chem. 1998, 41, pp. 3314-3324.

Barratt, J.D., et al., "The computational prediction of toxicity," Current Opinion Chemical Biology, 2001, 5(4): pp. 383-388.

Baxter, J.D., et al., "Structure-Based Design and Synthesis of a Thyroid Hormoneo Receptor (TR) Antagonist," Endocrinology, 2002, 143(2): pp. 517-524.

Bourguet, W., et al., "Crystal Structure of a Heterodimeric Complex of RAR and RXR Ligand-Binding Domains," Molecular Cell, vol. 5., Feb. 2000, pp. 289-298.

Bourguet, W., et al., "Crystal structure of the ligand-binding domian of the human nuclear receptor RXR-a," Nature, vol. 375, Jun. 1995, pp. 377-382.

Bourguet, W., et al., "Nuclear receptor ligand-binding domains: three-dimensional structures, molecular interactions and pharmacological implications," Trends Pharmacol Sci., Oct. 2000, vol. 21, pp. 381-338.

Brzozowski, A.M., et al., "Molecular basis of agonism and antagonism in the oestrogen receptor," Nature, vol. 289, Oct. 1997, pp. 753-758.

Casanova, Jr., et al., "Photoaffinity Labeling of Thyroid Hormone Nuclear Receptors," The Journal of Biological Chemistry, vol. 259, No. 19, Oct. 10, 1984, pp. 12084-12091.

Chambon, Pierre, "The molecular and genetic dissection of the retinoid signalling pathyway*," Gene, 135 (1993) pp. 223-228.

Darimont, B.D., et al., "Structure and specificity of nuclear receptor-coactivator interactions," Genes Dev., 12, (1998), pp. 3343-3356.

Egea, P.F., et al., "Crystal structure of the human RXRa ligand-binding domain bound to its nature ligand: 9-cis retinoic acid," The EMBO Journal, vol. 19, No. 11, 2000, pp. 2592-2601.

Evans, R.M., "The Steroid and Thyroid Hormone Receptor Superfamily," Science, 240, 1988, pp. 889-895.

Filikov, A.V., et al., "Identification of ligands for RNA targets via structure-based virtual screening: HIV-1 TAR," Journal of Computer-Aided Molecular Design, vol. 14, 2000, pp. 593-610.

Forrest, D., et al., "Thyroid hormone receptor beta is essential for development of auditory function," Nature Genetics, vol. 13, Jul. 1996, pp. 354-357.

Greene, Nigel, "Computer systems for the prediction of toxicity: an update," Advanced Drug Delivery Reviews, 54 (2002) pp. 417-431.

Labrie, F., "Mechanism of Action and Pure Antiandrogenic Properties of Flutamide," Cancer, 1993, 72: pp. 3816-3827.

Dangsheng, L., et al., "NRIF3 Is a Novel Coactivator Mediataing Functional Specificity of Nuclear Hormone Receptors," Molecular and Cellular Biology, Oct. 1999, pp. 7191-7202.

Lipinski, C.A., et al., "Experimental and computational approaches to estimate solubility and permeability in drug, discovery and development settings," Advanced Drug Delivery Reviews, 46 (2001) pp. 3-26.

Macchia, P.E., et al., "Increased sensitivity to thyroid hormone in mice with complete deficiency of thyroid hormone recepto alpha," PNAS, Jan. 2, 2001, vol. 98, No. 1, pp. 349-354.

McGovern, S.L., et al., "A Common Mechanism Underlying Promiscuous Inhibitors from Virtual and High-Throughout Screening," J. Med. Chem. 2002, 45, pp. 1712-1722.

Moras, D., et al., "The nuclear receptor ligand-binding domain: structure and function," Current Opinion in Cell Biology, 1998, 10: pp. 384-391.

Nolte, Robert T., et al., "Ligand binding and co-activator assembly of the peroxisome proliferator-activated receptory-y," Nature, Sep. 1998, vol. 395, pp. 137-143.

Olefsky, J.M., et al., "PPARy and the Treatment of Insulin Resistance," TEM, vol. 11, No. 9, 2000, pp. 362-368.

Onate, S.A., et al., "Sequence and Characterization of a Coactivator for the Steroid Hormone Receptor Superfamily," Science, vol. 270, Nov. 24, 1995, pp. 1354-1357.

Pike, A.C.W., et al., "Structure of the ligand-binding domain of oestrogen receptor beta in the presence of a partial agonist and a full antagonist," The EMBO Journal, vol. 18, No. 17, 1999, pp. 4608-4818.

Pike, A.C.W., et al., "Structure Insights into the Mode of Action of a Pure Antiestrogen," Structure, vol. 9, Feb. 2011, pp. 145-153.

Powers, C.A., et al., "TLS (Translocated-in-Liposarcoma) Is a High-Affinity Interactor for Steroid, Thyroid Hormone, and Retinoid Receptors," Molecular Endocrinology, 1998, vol. 12, pp. 4-18.

Raaka, B.M., et al., "The Glucocorticoid Receptor in GH1 Cells," The Journal of Biological Chemistry, vol. 258, No. 1, Jan. 10, 1983, pp. 417-425.

Sadowski, J., et al., "A Scoring Scheme for Discriminating between Drugs and Nondrugs," The Journal of Med. Chem., 1998, vol. 41, pp. 3325-3329.

Samuels, H.H., et al., "Thyroid Hormone Action in Cell Culture: Demonstration of Nuclear Receptors in Intact Cells and Isoloated Nuclei," Proc. Nat. Acad. Sci. USA, vol. 70, No. 12, Dec. 1973, pp. 348-3492.

Schapira, M., et al., "In silico discovery of noval Retinoic Acid Receptor agonist structures," BMC Structural Biology, 2001, vol. 1, No. 1, p. 1.

Schapira, M., et al., "Rational discovery of novel nuclear hormone receptor antagonists," PNAS, vol. 97, No. 3, Feb. 1, 2000, pp. 1008-1013.

Shiau, A.K., et al., "The Structural Basis of Estrogen Receptor/Coactivator Recognition and the Antagonism of This Interaction by Tamoxifen," Cell, vol. 95, Dec. 23, 1998, pp. 927-937.

Shiau, A.K., et al., "Structural characterization of a subtype-selective ligand reveals a novel mode of estrogen receptor antagonism," Nature Structural Biology, vol. 9, No. 5, May 2002, pp. 359-364.

Steinmetz, A.C., et al., "Binding of Ligands and Activation of Transcription by Nuclear Receptors," Annu. Rev. Biophys. Biomol. Struct., vol. 30, 2001, pp. 329-359.

Strynadka, N.C., et al., "Molecular docking programs sucessfully predict the binding of a Beta-lactamase inhibitory protein to TEM-1 Beta-lactamase," Nature Structural Biology, vol. 3, No. 3, Mar. 1996, pp. 233-239.

Takeuchi, Y., et al., "Steroid Recptor Coactivator-1 Deficiency Causes Variable Alterations in the Modulation of T3-Regulated Transcription of Genes in Vivo," Endocrinology, vol. 143, No. 4, 2002, pp. 1346-1352.

Totrov, M., et al., "Flexible Protein-Ligand Docking by Global Energy Optimization in Internal Coordinates," Proteins, Suppl. 1, (1997), pp. 215-220.

Veber, D.F., et al., "Molecular Properties That Influence the Oral Bioavailability of Drug Candidates," J. Med. Chem., vol. 45, 2002, pp. 2615-2623.

Weatherman, R.V., et al., "Nuclear-Recptor Ligands and Ligand-Binding Domains," Annu. Rev. Biochem., vol. 68, 1999, pp. 559-581.

Weiss, R.E., et al., "Thyroid function and effect of aging in combined hetero/homozygous mice deficient in thyroid hormone receptors alpha and beta genes," J. Endocrinol., vol. 172, No. 1, 2002, pp. 177-185.

Weiss, R.E., et al., "Mice deficient in the steroid receptor co-activator 1 (SRC-1) are resistant to thyroid hormone," The EMBO Journal, vol. 18, No. 7, 1999, pp. 1900-1904.

Weiss, R.E., et al., "Resistance to Thyroid Hormone," Rev. Endocr. Metab. Disord., vol. 1, No. 12, 2000, pp. 97-108.

Wikstrom, L., et al., "Abnormal heart rate and body temperature in mice lacking thyroid hormone receptor alpha-1," The EMBO Journal, vol. 17, No. 2, 1998, pp. 455-461.

Xu, H.E., et al., "Structural basis for antagonis-mediated recruitment of nucelar co-repressors by PPARa," Nature, vol. 415, Feb. 14, 2002, pp. 813-817.

Yen, P.M., "Physiological and Molecular Basis of Thyroid Hormone Action," Physiological Reviews, vol. 81, No. 3, Jul. 2001, pp. 1097-1142.

* cited by examiner

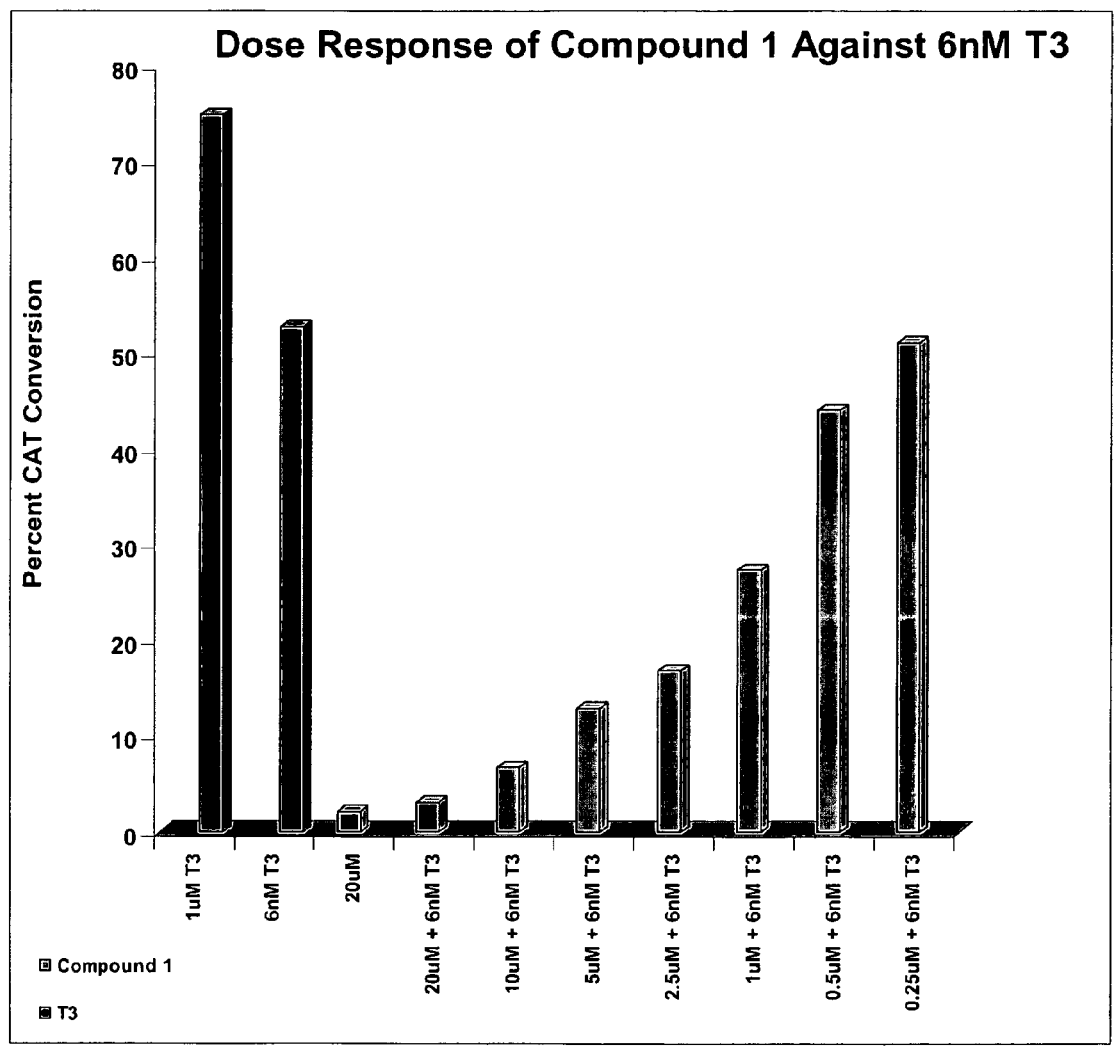

HYDRAZIDE COMPOUNDS AS THYROID HORMONE RECEPTOR MODULATORS AND USES THEREOF

CROSS REFERENCE TO RELATED APPLICATIONS

The present application is a National Stage Application claiming the priority of co-pending PCT Application No. PCT/US2008/005031 filed Apr. 18, 2008, which in turn, claims priority from U.S. Provisional Applications Serial No.(s) 60/925,020, filed Apr. 18, 2007; 60/923,964 filed Apr. 18, 2007; and 60/923,995 filed Apr. 18, 2007. Applicants claim the benefits of 35 U.S.C. §120 as to the PCT application and priority under 35 U.S.C. §119(e) as to the said Provisional applications, and the entire disclosures of all applications are incorporated herein by reference in their entireties.

STATEMENT OF GOVERNMENTAL SUPPORT

The research leading to the present invention was supported, at least in part, by National Institute of Health (NIH) Grant Nos. DK16636 and DK059041. Accordingly, the United States Government may have certain rights in the invention.

FIELD OF THE INVENTION

The invention relates to compounds and pharmaceutical compositions, and to the uses thereof, that are effective for treating conditions characterized by aberrant activity of the thyroid gland, such as overproduction of thyroid hormone, and particularly to such compounds as may function as thyroid hormone receptor antagonists.

BACKGROUND OF THE INVENTION

Overproduction of thyroid hormone (hyperthyroidism or thyrotoxicosis) is an extremely common clinical entity caused by a number of different pathological conditions of the thyroid gland. Approximately 0.5% of women will experience some clinical manifestation of hyperthyroidism in their lifetime (a frequency 3 to 5 times higher than that occurring in men), with potentially life-threatening effects on the cardiovascular system, including cardiac arrhythmias, heart failure, angina and myocardial infarction, particularly in the j elderly[1-3].

The treatment of hyperthyroidism has essentially remained unchanged for the past thirty years, and includes the use of radioactive iodine, surgery, or the use of anti-thyroid drugs, such as propylthiouracil, that inhibit thyroid hormone synthesis by blocking the iodination of thyroglobulin1-3. Each approach has its own intrinsic limitations and/or side effects. Propylthiouracil and related drugs, which block thyroid hormone synthesis, act slowly and can take up to six to eight weeks to fully deplete the thyroid gland and intrathyroidal stores of iodinated thyroglobulin, during which time hyperthyroidism can have severe consequences in certain individuals. Radiochemical destruction of thyroid tissues by iodine may require four to six months to be fully effective while surgical thyroidectomy must be preceded with anti-thyroid drugs to prevent life threatening complications such as thyroid storm.

The identification of thyroid hormone receptor ("TR") antagonists could play an important role in the future treatment of hyperthyroidism. Such molecules would act rapidly by directly antagonizing the effect of thyroid hormone at the receptor level, a significant improvement for individuals with hyperthyroidism who require surgery, have cardiac disease, or life threatening thyrotoxic storm.

As described herein, the present invention addresses the need for novel agents capable of modulating thyroid hormone receptor activity.

SUMMARY OF THE INVENTION

The present invention concerns the usage of ligands having the effect of antagonizing TR as pharmaceutical agents. The compounds of interest are ligands capable of bonding to TR. These compounds and pharmaceutical compositions containing them are useful for the treatment of conditions such as hyperthyroidism which are characterized by an overproduction of TR by the thyroid gland. Additionally, the invention includes a method for the computer based screening, optimization, in vitro testing, and synthesis of novel compounds having TR antagonist activity using a library that may include commercially available starting compounds.

The focus of the present invention is, therefore, directed to the identification of the previously unidentified TR modulators and their use in modulating thyroid gland activity, and particularly, conditions such as hyperthyroidism. Accordingly, the present invention covers a group of novel TR modulators within its scope.

In a first aspect of the invention, the TR modulators of the present invention are represented by a formula selected from:

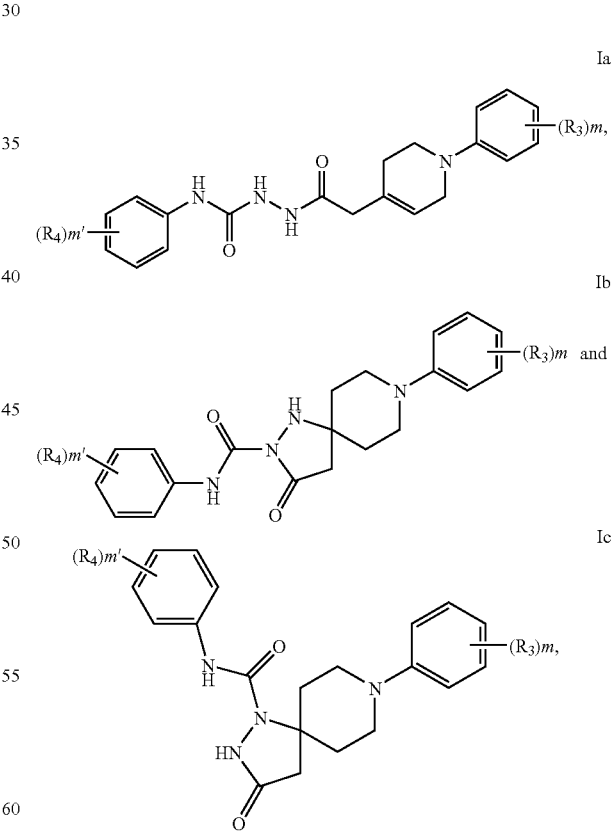

or a pharmaceutically acceptable salt, solvate or prodrug thereof, and stereoisomers, tautomers and isotopic variants thereof; and wherein:

each of $R^3$ and $R^4$ are independently H, substituted or unsubstituted alkyl, substituted or unsubstituted alkoxy, substituted or unsubstituted amino, substituted or unsubstituted amido, NHSO$_2$-alkyl, halo, or nitro; and each of m and m' are independently selected from 0-4.

In a second aspect of the invention, compounds are disclosed that are TR modulators, having a formula selected from:

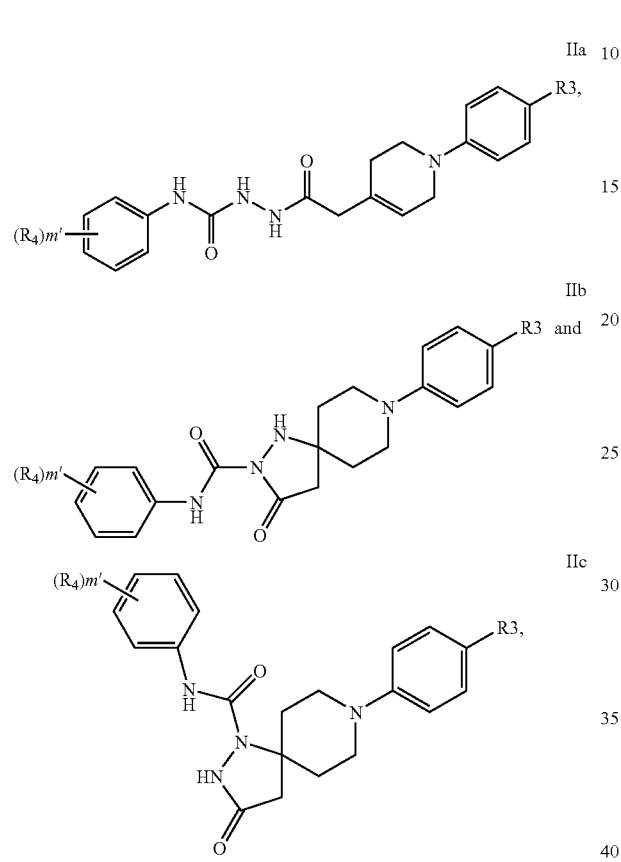

or a pharmaceutically acceptable salt, solvate or prodrug thereof, and stereoisomers, tautomers and isotopic variants thereof; and wherein:

each of R$^3$ and R$^4$ are independently H, substituted or unsubstituted alkyl, substituted or unsubstituted alkoxy, substituted or unsubstituted amino, substituted or unsubstituted amido, NHSO$_2$-alkyl, halo, or nitro; and m' is selected from 0-4.

In a third aspect of the invention, compounds are disclosed that are TR modulators, having a formula selected from:

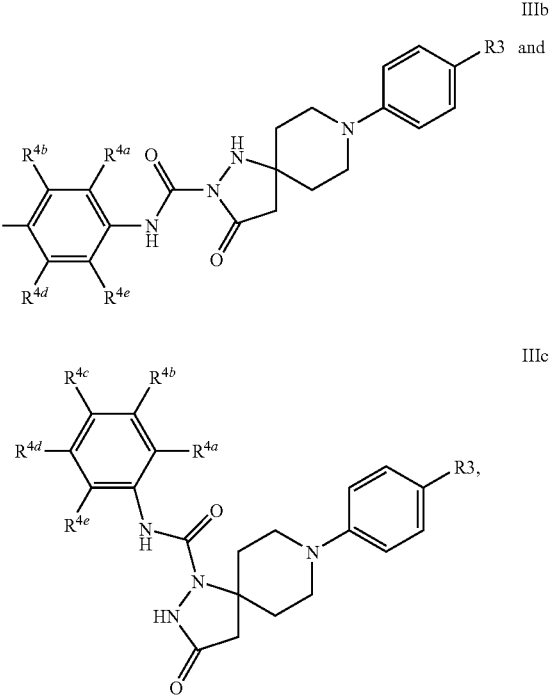

or a pharmaceutically acceptable salt, solvate or prodrug thereof, and stereoisomers, tautomers and isotopic variants thereof; and wherein:

each of R$^3$ and R$^{4a-e}$ are independently H, substituted or unsubstituted alkyl, substituted or unsubstituted alkoxy, substituted or unsubstituted amino, substituted or unsubstituted amido, NHSO$_2$-alkyl, halo, or nitro.

In a fourth aspect, compounds are disclosed that are TR modulators, having a formula selected from:

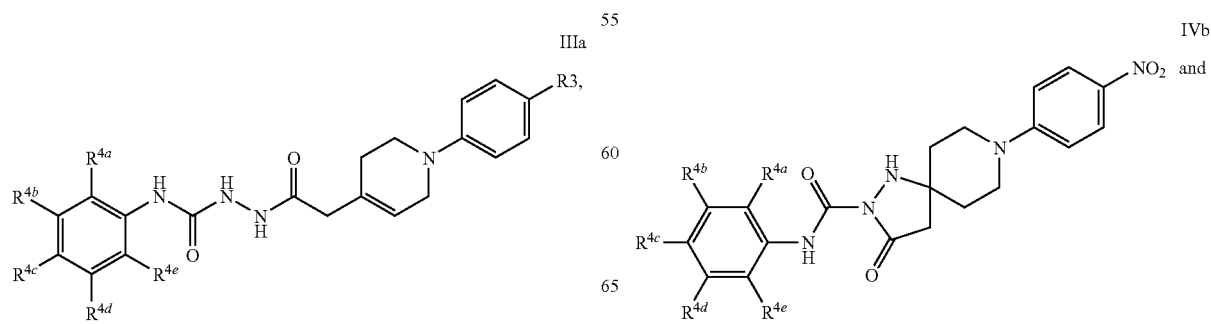

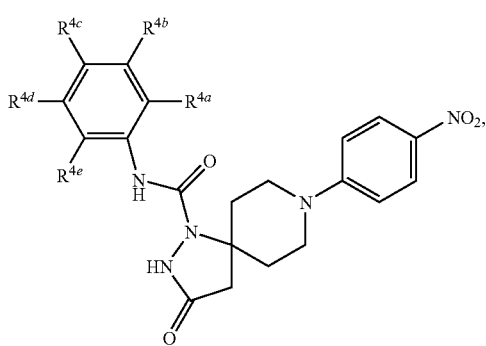

IVc or a pharmaceutically acceptable salt, solvate or prodrug thereof, and stereoisomers, tautomers and isotopic variants thereof; and wherein:

each of $R^{4a-e}$ are independently H, substituted or unsubstituted alkyl, substituted or unsubstituted alkoxy, substituted or unsubstituted amino, substituted or unsubstituted amido, $NHSO_2$-alkyl, halo, or nitro.

In another aspect, compounds are disclosed that are TR modulators, having a formula selected from:

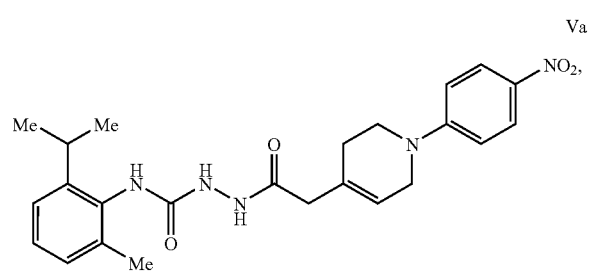

Va

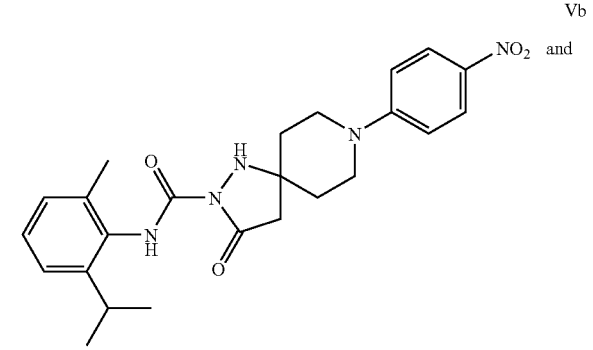

Vb and

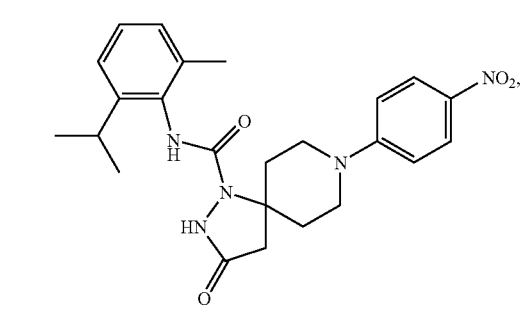

Vc or a pharmaceutically acceptable salt, solvate or prodrug thereof, and stereoisomers, tautomers and isotopic variants thereof.

In addition to the above embodiments, compounds having variant structures are recited herein, in the ensuing description.

In a further aspect, the invention provides a method for the identification, screening, optimization of selectivity of, and synthesis of compounds capable of antagonizing the effects of TR, wherein the method comprises the steps of
i) selecting a compound of the present invention, such as a compound selected from the group consisting of Formulae Ia-Vc;
ii) generating a virtual library of derivatives of the compound chosen in step i);
iii) screening said library in silico;
iv) chemically synthesizing at least one compound screened in iii); and
v) testing in vitro at least one compound synthesized in iv).

In a still further aspect, the invention provides original ligands with TR antagonist activity in the μM range and sub-μM range.

In another aspect, the invention provides pharmaceutical compositions comprising one or more compounds of the invention, effective for the treatment of conditions such as hyperthyroidism and thyrotoxicosis characterized by overproduction of thyroid hormone wherein the compositions act by antagonizing TR.

In a further aspect, the invention provides methods for modulation a process mediated by thyroid hormone nuclear receptors by administering to a human a compound or composition according to the invention that is capable of antagonizing TR.

In addition to the methods of treatment set forth above, the present invention extends to the use of any of the compounds of the invention for the preparation of medicaments that may be administered for such treatments, as well as to such compounds for the treatments disclosed and specified.

Other objects and advantages will be apparent to those skilled in the art from a consideration of the ensuing detailed description, taken in conjunction with the following illustrative drawings.

BRIEF DESCRIPTION OF THE DRAWINGS

FIG. 1 is a graph presenting the results of an in vitro assay of the activity of a compound of the invention.

DETAILED DESCRIPTION OF THE INVENTION

The invention relates to the discovery of original ligands with TR antagonist activity in the μM range and sub-μM range, to pharmaceutical compositions containing such compounds, and to the uses thereof. The activity of the thyroid hormones, L-thyroxin (T4) and L-triiodothyronine (T3), is mediated by the thyroid hormone receptor ("TR")[45,50,51]. The TRs are members of the nuclear hormone receptor (NR) superfamily that also includes receptors for steroid hormones, retinoids, and 1,25-dihydroxy-vitamin D3[5-7]. These receptors are transcription factors that can regulate expression of specific genes in various tissues, and are targets for widely used drugs, such as tamoxifen, an estrogen receptor (ER) partial antagonist, flutamide, an anti-androgen, or rosiglitazone, a peroxisome proliferator activated receptor-γ (PPARγ) agonist (Dees 1998) (Olefsky 2000).

Several different isoforms of TR (TR-α1, TR-β1 and TR-β2) are differentially expressed in various tissues and have been described (Lazar 1993). Gene knockout studies in mice indicate that the TRβ isoforms plays a role in the development of the auditory system and in the negative feedback of thyroid stimulating hormone ("TSH") by T3 in the pituitary (Forrest 1996, Weiss 1997), while TRα modulates the effect of thyroid hormone on calorigenesis and on the cardiovascular system (Wikstrom 1998).

In a preferred embodiment, compounds according to the invention act to antagonize TR. Previous expertise in the structure/function of NRs facilitated the construction of a TR model in its antagonist-bound conformation.

DEFINITIONS

The following terms are intended to have the meanings presented therewith below and are useful in understanding the description and intended scope of the present invention.

When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated substituted is to be defined as set out below. It should be further understood that the terms "groups" and "radicals" can be considered interchangeable when used herein.

The articles "a" and "an" may be used herein to refer to one or to more than one (i.e. at least one) of the grammatical objects of the article. By way of example "an analogue" means one analogue or more than one analogue.

'Acyl' refers to a radical —C(O)$R^{20}$, where $R^{20}$ is hydrogen, alkyl, cycloalkyl, cycloheteroalkyl, aryl, arylalkyl, heteroalkyl, heteroaryl or heteroarylalkyl as defined herein. Representative examples include, but are not limited to, formyl, acetyl, cyclohexylcarbonyl, cyclohexylmethylcarbonyl, benzoyl and benzylcarbonyl. Exemplary 'acyl' groups include —C(O)H, —C(O)—$C_1$-$C_8$ alkyl, —C(O)—$(CH_2)_t(C_6$-$C_{10}$ aryl), —C(O)—$(CH_2)_t(C_5$-$C_{10}$ heteroaryl), —C(O)—$(CH_2)_t(C_3$-$C_{10}$ cycloalkyl), and —C(O)—$(CH_2)_t(C_5$-$C_{10}$ heterocycloalkyl), wherein t is an integer from 0 to 4 and any aryl, heteroaryl, cycloalkyl or heterocycloalkyl groups present, may themselves be substituted by $C_1$-$C_4$ alkyl, halo, $C_1$-$C_4$ alkoxy, $C_{1\text{-}4}$ haloalkyl, $C_1$-$C_4$ hydroxyalkyl, or $C_1$-$C_4$ haloalkoxy or hydroxy.

'Acylamino' refers to a radical —$NR^{21}C(O)R^{22}$, where $R^{21}$ is hydrogen, alkyl, cycloalkyl, cycloheteroalkyl, aryl, arylalkyl, heteroalkyl, heteroaryl or heteroarylalkyl and $R^{22}$ is hydrogen, alkyl, alkoxy, cycloalkyl, cycloheteroalkyl, aryl, arylalkyl, heteroalkyl, heteroaryl or heteroarylalkyl, as defined herein. Representative examples include, but are not limited to, formylamino, acetylamino, cyclohexylcarbonylamino, cyclohexylmethyl-carbonylamino, benzoylamino and benzylcarbonylamino. Exemplary 'acylamino' groups include —$NR^{21}C(O)$—$C_1$-$C_8$ alkyl, —$NR^{21}C(O)$—$(CH_2)_t(C_6$-$C_{10}$ aryl), —$NR^{21}C(O)$—$(CH_2)_t(C_5$-$C_{10}$ heteroaryl), —$NR^{21}C(O)$—$(CH_2)_t(C_3$-$C_{10}$ cycloalkyl), and —$NR^{21}C(O)$—$(CH_2)_t(C_5$-$C_{10}$ heterocycloalkyl), wherein t is an integer from 0 to 4, each $R^{21}$ independently represents H or $C_1$-$C_6$ alkyl and any aryl, heteroaryl, cycloalkyl or heterocycloalkyl groups present, may themselves be substituted by $C_1$-$C_4$ alkyl, halo, $C_1$-$C_4$ alkoxy, $C_{1\text{-}4}$ haloalkyl, $C_1$-$C_4$ hydroxyalkyl, or $C_1$-$C_4$ haloalkoxy or hydroxy.

'Acyloxy' refers to the group —OC(O)$R^{23}$ where $R^{23}$ is hydrogen, alkyl, aryl or cycloalkyl. Exemplary 'acyloxy' groups include OC(O)—$C_1$-$C_8$ alkyl, —OC(O)—$(CH_2)_t(C_6$-$C_{10}$ aryl), —OC(O)—$(CH_2)_t(C_5$-$C_{10}$ heteroaryl), —OC(O)—$(CH_2)_t(C_3$-$C_{10}$ cycloalkyl), and —OC(O)—$(CH_2)_t(C_5$-$C_{10}$ heterocycloalkyl), wherein t is an integer from 0 to 4 and any aryl, heteroaryl, cycloalkyl or heterocycloalkyl groups present, may themselves be substituted by $C_1$-$C_4$ alkyl, halo, $C_1$-$C_4$ alkoxy, $C_{1\text{-}4}$ haloalkyl, $C_1$-$C_4$ hydroxyalkyl, or $C_1$-$C_4$ haloalkoxy or hydroxy.

'Alkoxy' refers to the group —$OR^{24}$ where $R^{24}$ is alkyl. Particular alkoxy groups include, by way of example, methoxy, ethoxy, n-propoxy, isopropoxy, n-butoxy, tert-butoxy, sec-butoxy, n-pentoxy, n-hexoxy and 1,2-dimethylbutoxy. Particular alkoxy groups are lower alkoxy, i.e. with between 1 and 6 carbon atoms.

'Substituted alkoxy' refers to an alkoxy group substituted with one or more of those groups recited in the definition of "substituted" herein, and particularly refers to an alkoxy group having 1 or more substituents, for instance from 1 to 5 substituents, and particularly from 1 to 3 substituents, in particular 1 substituent, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, heteroaryl, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—. Exemplary 'substituted alkoxy' groups include —O—$(CH_2)_t$ $(C_6$-$C_{10}$ aryl), —O—$(CH_2)_t(C_5$-$C_{10}$ heteroaryl), —O—$(CH_2)_t(C_3$-$C_{10}$ cycloalkyl), and —O—$(CH_2)_t(C_5$-$C_{10}$ heterocycloalkyl), wherein t is an integer from 0 to 4 and any aryl, heteroaryl, cycloalkyl or heterocycloalkyl groups present, may themselves be substituted by $C_1$-$C_4$ alkyl, halo, $C_1$-$C_4$ alkoxy, $C_1$-$C_4$ haloalkyl, $C_1$-$C_4$ hydroxyalkyl, or $C_1$-$C_4$ haloalkoxy or hydroxy.

'Alkoxycarbonylamino' refers to the group —$NR^{25}C(O)OR^{26}$, where $R^{25}$ is hydrogen, alkyl, aryl or cycloalkyl, and $R^{26}$ is alkyl or cycloalkyl.

'Alkyl' means straight or branched aliphatic hydrocarbon having 1 to about 20 carbon atoms. A particular alkyl has 1 to about 12 carbon atoms. A further particular alkyl is lower alkyl which has 1 to 6 carbon atoms. Other particular alkyls are groups such as methyl, ethyl and propyl. Branched means that one or more lower alkyl groups such as methyl, ethyl or propyl is attached to a linear alkyl chain. The term $C_1$-$C_6$ alkyl includes both branched and straight chain groups, exemplary straight chain groups include ethyl, propyl, butyl, exemplary branched chain groups include isopropyl, isoamyl, and the like.

'Substituted alkyl' refers to an alkyl group substituted with one or more of those groups recited in the definition of "substituted" herein, and particularly refers to an alkyl group having 1 or more substituents, for instance from 1 to 5 substituents, and particularly from 1 to 3 substituents, in particular 1 substituent, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, heteroaryl, keto, nitro, thioalkoxy, substituted thioalkoxy, thioaryloxy, thioketo, thiol, alkyl-S(O)—, aryl-S(O)—, alkyl-S(O)$_2$—, and aryl-S(O)$_2$—. In a particular embodiment 'substituted alkyl' refers to a $C_1$-$C_6$ alkyl group substituted with halo, cyano, nitro, trifluoromethyl, trifluoromethoxy, azido, —NR'''SO$_2$R'', —SO$_2$NR''R''', —C(O)R'', —C(O)OR'', —OC(O)R'', —NR'''C(O)R'', —C(O)NR''R''', —NR''R''', or —(CR'''R''')$_m$OR'''; wherein each R'' is independently selected from H, $C_1$-$C_8$ alkyl, —$(CH_2)_t(C_6$-$C_{10}$ aryl), —$(CH_2)_t(C_5$-$C_{10}$ heteroaryl), —(CH$_2$)$_t$(C$_3$-C$_{10}$ cycloalkyl), and —(CH$_2$)$_t$(C$_5$-C$_{10}$ heterocycloalkyl), wherein t is an integer from 0 to 4 and any aryl, heteroaryl, cycloalkyl or heterocycloalkyl groups present, may themselves be substituted by C$_1$-C$_4$ alkyl, halo, C$_1$-C$_4$ alkoxy, C$_{1-4}$ haloalkyl, C$_1$-C$_4$ hydroxyalkyl, or C$_1$-C$_4$ haloalkoxy or hydroxy. Each of R''' and R'''' independently represents H or C$_1$-C$_6$ alkyl.

'Alkylene' refers to divalent alkene radical groups having 1 to 11 carbon atoms and more particularly 1 to 6 carbon atoms which can be straight-chained or branched. This term is exemplified by groups such as methylene (—CH$_2$—), ethylene (—CH$_2$CH$_2$—) and the propylene isomers (e.g., —CH$_2$CH$_2$CH$_2$— and —CH(CH$_3$)CH$_2$—).

'Substituted alkylene' refers to an alkylene group substituted with one or more of those groups recited in the definition of 'substituted' herein, and particularly refers to an alkylene group having 1 or more substituents, for instance from 1 to 5 substituents, and particularly from 1 to 3 substituents, in particular 1 substituent.

'Alkenyl' refers to monovalent olefinically (unsaturated) hydrocarbon groups preferably having 2 to 11 carbon atoms, particularly, from 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl n-propenyl (—CH$_2$CH=CH$_2$), isopropenyl (—C(CH$_3$)=CH$_2$), vinyl and substituted vinyl.

'Substituted alkenyl' refers to an alkenyl group substituted with one or more of those groups recited in the definition of 'substituted' herein, and particularly refers to an alkenyl group having 1 or more substituents, for instance from 1 to 5 substituents, and particularly from 1 to 3 substituents, in particular 1 substituent.

'Alkenylene' refer to divalent olefinically (unsaturated) hydrocarbon groups particularly having up to about 11 carbon atoms and more particularly 2 to 6 carbon atoms which can be straight-chained or branched and having at least 1 and particularly from 1 to 2 sites of olefinic unsaturation. This term is exemplified by groups such as ethenylene (—CH=CH—) and the propenylene isomers (e.g., —CH=CHCH$_2$— and —C(CH$_3$)=CH— and —CH=C(CH$_3$)—).

'Alkynyl' refers to acetylenically or alkynically (unsaturated) hydrocarbon groups particularly having 2 to 11 carbon atoms and more particularly 2 to 6 carbon atoms which can be straight-chained or branched and having at least 1 and particularly from 1 to 2 sites of alkynyl unsaturation. Particular non-limiting examples of alkynyl groups include acetylenic, ethynyl (—C≡CH), and propargyl (—CH$_2$C≡CH).

'Substituted alkynyl' refers to an alkynyl group substituted with one or more of those groups recited in the definition of "substituted" herein, and particularly refers to an alkynyl group having 1 or more substituents, for instance from 1 to 5 substituents, and particularly from 1 to 3 substituents, in particular 1 substituent.

'Alkanoyl' or 'acyl' as used herein refers to the group R$^{27}$—C(O)—, where R$^{27}$ is hydrogen or alkyl as defined above.

'Aryl' refers to a monovalent aromatic hydrocarbon group derived by the removal of one hydrogen atom from a single carbon atom of a parent aromatic ring system. In particular aryl refers to an aromatic ring structure, mono-cyclic or polycyclic that includes from 5 to 12 ring members, more usually 5 to 10. Where the aryl group is a monocyclic ring system it preferentially contains 6 carbon atoms. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene and trinaphthalene. Particularly aryl groups include phenyl, naphthyl, indenyl, and tetrahydronaphthyl. The term 'aryl' includes 'bicycloaryl' as defined below.

'Bicycloaryl' refers to a monovalent aromatic hydrocarbon group derived by the removal of one hydrogen atom from a single carbon atom of a parent bicycloaromatic ring system. Typical bicycloaryl groups include, but are not limited to, groups derived from indane, indene, naphthalene and tetrahydronaphthalene. Particularly, an aryl group comprises from 8 to 11 carbon atoms.

'Substituted aryl' refers to an aryl group substituted with one or more of those groups recited in the definition of 'substituted' herein, and particularly refers to an aryl group that may optionally be substituted with one or more substituents, for instance from 1 to 5 substituents, particularly from 1 to 3 substituents, and in particular one substituent.

'Fused aryl' refers to an aryl having two of its ring carbon in common with a second aryl ring or with an aliphatic ring.

'Alkaryl' or 'arylalkyl' refers to an aryl group, as defined above, substituted with one or more alkyl groups, as defined above.

'Substituted aralkyl' or 'substituted arylalkyl' refers to an alkyl group, as defined above, substituted with one or more aryl groups, as defined above.

'Aryloxy' refers to —O-aryl groups wherein 'aryl' is as defined above.

'Alkylamino' refers to the group alkyl-NR$^{28}$R$^{29}$, wherein each of R$^{28}$ and R$^{29}$ are independently selected from hydrogen and alkyl.

'Arylamino' refers to the group aryl-NR$^{30}$R$^{31}$, wherein each of R$^{30}$ and R$^{31}$ are independently selected from hydrogen, aryl and heteroaryl.

'Alkoxyamino' refers to a radical —N(H)OR$^{32}$ where R$^{32}$ represents an alkyl or cycloalkyl group as defined herein.

'Alkoxycarbonyl' refers to a radical —C(O)-alkoxy where alkoxy is as defined herein. Exemplary 'alkoxycarbonyl' groups include C(O)O—C$_1$-C$_8$ alkyl, —C(O)O—(CH$_2$)$_t$(C$_6$-C$_{10}$ aryl), —C(O)O—(CH$_2$)$_t$(C$_5$-C$_{10}$ heteroaryl), —C(O)O—(CH$_2$)$_t$(C$_3$-C$_{10}$ cycloalkyl), and —C(O)O—(CH$_2$)$_t$(C$_5$-C$_{10}$ heterocycloalkyl), wherein t is an integer from 0 to 4 and any aryl, heteroaryl, cycloalkyl or heterocycloalkyl groups present, may themselves be substituted by C$_1$-C$_4$ alkyl, halo, C$_1$-C$_4$ alkoxy, C$_{1-4}$ haloalkyl, C$_1$-C$_4$ hydroxyalkyl, or C$_1$-C$_4$ haloalkoxy or hydroxy.

'Alkylarylamino' refers to a radical —NR$^{33}$R$^{34}$ where R$^{33}$ represents an alkyl or cycloalkyl group and R$^{34}$ is an aryl as defined herein.

'Alkylsulfonyl' refers to a radical —S(O)$_2$R$^{35}$ where R$^{35}$ is an alkyl or cycloalkyl group as defined herein. Representative examples include, but are not limited to, methylsulfonyl, ethylsulfonyl, propylsulfonyl and butylsulfonyl.

'Alkylsulfinyl' refers to a radical —S(O)R$^{35}$ where R$^{35}$ is an alkyl or cycloalkyl group as defined herein. Representative examples include, but are not limited to, methylsulfinyl, ethylsulfinyl, propylsulfinyl and butylsulfinyl.

'Alkylthio' refers to a radical —SR$^{35}$ where R$^{35}$ is an alkyl or cycloalkyl group as defined herein that may be optionally substituted as defined herein. Representative examples include, but are not limited to, methylthio, ethylthio, propylthio and butylthio. Exemplary 'alkylthio' groups include S—C$_1$-C$_8$ alkyl, —S—(CH$_2$)$_t$(C$_6$-C$_{10}$ aryl), —S—(CH$_2$)$_t$(C$_5$-C$_{10}$ heteroaryl), —S—(CH$_2$)$_t$(C$_3$-C$_{10}$ cycloalkyl), and —S—(CH$_2$)$_t$(C$_5$-C$_{10}$ heterocycloalkyl), wherein t is an integer from 0 to 4 and any aryl, heteroaryl, cycloalkyl or heterocycloalkyl groups present, may themselves be substituted by C$_1$-C$_4$ alkyl, halo, C$_1$-C$_4$ alkoxy, C$_1$-C$_4$ haloalkyl, C$_1$-C$_4$ hydroxyalkyl, or C$_1$-C$_4$ haloalkoxy or hydroxy.

'Amino' refers to the radical —NH$_2$.

'Substituted amino' refers to an amino group substituted with one or more of those groups recited in the definition of 'substituted' herein, and particularly refers to the group —N(R$^{36}$)$_2$ where each R$^{36}$ is independently selected from the group consisting of hydrogen, alkyl, substituted alkyl, alkenyl, substituted alkenyl, alkynyl, substituted alkynyl, aryl, cycloalkyl, substituted cycloalkyl, and where both R groups are joined to form an alkylene group. When both R groups are hydrogen, —N(R$^{36}$)$_2$ is an amino group. Exemplary 'substituted amino' groups include =NR$^{36}$—C$_1$-C$_8$ alkyl, —NR$^{36}$—(CH$_2$)$_t$(C$_6$-C$_{10}$ aryl), —NR$^{36}$—(CH$_2$)$_t$(C$_5$-C$_{10}$ heteroaryl), —NR$^{36}$—(CH$_2$)$_t$(C$_3$-C$_{10}$ cycloalkyl), and —NR$^{36}$—(CH$_2$)$_t$(C$_5$-C$_{10}$ heterocycloalkyl), wherein t is an integer from 0 to 4, each R$^{36}$ independently represents H or C$_1$-C$_6$ alkyl and any aryl, heteroaryl, cycloalkyl or heterocycloalkyl groups present, may themselves be substituted by C$_1$-C$_4$ alkyl, halo, C$_1$-C$_4$ alkoxy, C$_1$-C$_4$ haloalkyl, C$_1$-C$_4$ hydroxyalkyl, or C$_1$-C$_4$ haloalkoxy or hydroxy.

'Aminocarbonyl' refers to the group —C(O)NR$^{37}$R$^{37}$ where each R$^{37}$ is independently hydrogen, alkyl, aryl and cycloalkyl, or where the R$^{37}$ groups are joined to form an alkylene group.

'Aminocarbonylamino' refers to the group —NR$^{38}$C(O)NR$^{38}$R$^{38}$ where each R$^{38}$ is independently hydrogen, alkyl, aryl or cycloalkyl, or where two R groups are joined to form an alkylene group.

'Aminocarbonyloxy' refers to the group —OC(O)NR$^{39}$R$^{39}$ where each R$^{39}$ is independently hydrogen, alkyl, aryl or cycloalkyl, or where the R groups are joined to form an alkylene group.

'Arylalkyloxy' refers to an —O-arylalkyl radical where arylalkyl is as defined herein.

'Arylamino' means a radical —NHR$^{40}$ where R$^{40}$ represents an aryl group as defined herein.

'Aryloxycarbonyl' refers to a radical —C(O)—O-aryl where aryl is as defined herein.

'Arylsulfonyl' refers to a radical —S(O)$_2$R$^{41}$ where R$^{41}$ is an aryl or heteroaryl group as defined herein.

'Azido' refers to the radical —N$_3$.

'Carbamoyl' refers to the radical —C(O)N(R$^{42}$)$_2$ where each R$^{42}$ group is independently hydrogen, alkyl, cycloalkyl or aryl, as defined herein, which may be optionally substituted as defined herein. A particular carbamoyl group is —C(O)NH$_2$. Exemplary 'carbamoyl' groups include —C(O)NR$^{42}$—C$_1$-C$_8$ alkyl, —C(O)NR$^{42}$—(CH$_2$)$_t$(C$_6$-C$_{10}$ aryl), —C(O)NR$^{42}$—(CH$_2$)$_t$(C$_5$-C$_{10}$ heteroaryl), —C(O)NR$^{42}$—(CH$_2$)$_t$(C$_3$-C$_{10}$ cycloalkyl), and —C(O)NR$^{42}$—(CH$_2$)$_t$(C$_5$-C$_{10}$ heterocycloalkyl), wherein t is an integer from 0 to 4, each R$^{42}$ independently represents H or C$_1$-C$_6$ alkyl and any aryl, heteroaryl, cycloalkyl or heterocycloalkyl groups present, may themselves be substituted by C$_1$-C$_4$ alkyl, halo, C$_1$-C$_4$ alkoxy, C$_1$-C$_4$ haloalkyl, C$_1$-C$_4$ hydroxyalkyl, or C$_1$-C$_4$ haloalkoxy or hydroxy.

'Carboxy' refers to the radical —C(O)OH.

'Carboxyamino' refers to the radical —N(H)C(O)OH.

'Cycloalkyl' refers to cyclic non-aromatic hydrocarbyl groups having from 4 to about 7 carbon atoms and having a single cyclic ring, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl and 2-methylcyclooctyl.

'Substituted cycloalkyl' refers to a cycloalkyl group substituted with one or more of those groups recited in the definition of 'substituted' herein, and particularly refers to a cycloalkyl group having 1 or more substituents, for instance from 1 to 5 substituents, particularly from 1 to 3 substituents, and in particular, one substituent.

'Cycloalkoxy' refers to the group —OR$^{43}$ where R$^{43}$ is cycloalkyl. Such cycloalkoxy groups include, by way of example, cyclopentoxy and cyclohexoxy.

'Cycloalkenyl' refers to cyclic hydrocarbyl groups having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl and cyclopropenyl.

'Substituted cycloalkenyl' refers to a cycloalkenyl group substituted with one or more of those groups recited in the definition of 'substituted' herein, and particularly refers to a cycloalkenyl group having 1 or more substituents, for instance from 1 to 5 substituents, particularly from 1 to 3 substituents, and in particular, one substituent.

'Fused cycloalkenyl' refers to a cycloalkenyl having two of its ring carbon atoms in common with a second aliphatic or aromatic ring and having its olefinic unsaturation located to impart aromaticity to the cycloalkenyl ring.

'Cyanato' refers to the radical —OCN.

'Cyano' refers to the radical —CN.

'Dialkylamino' means a radical —NR$^{44}$R$^{45}$ where R$^{44}$ and R$^{45}$ independently represent an alkyl, substituted alkyl, aryl, substituted aryl, cycloalkyl, substituted cycloalkyl, cycloheteroalkyl, substituted cycloheteroalkyl, heteroaryl, or substituted heteroaryl group as defined herein.

'Ethenyl' refers to substituted or unsubstituted —(C=C)—.

'Ethylene' refers to substituted or unsubstituted —(C—C)—.

'Ethynyl' refers to —(C≡C)—.

'Halo' or 'halogen' refers to fluoro (F), chloro (Cl), bromo (Br) and iodo (I). Preferred halo groups are either fluoro or chloro.

'Hydrogen' means in the context of a substituent that —H is present at the compound position and also includes its isotope, deuterium.

'Hydroxy' refers to the radical —OH.

'Nitro' refers to the radical —NO$_2$.

'Substituted' refers to a group in which one or more hydrogen atoms are each independently replaced with the same or different substituent(s). Typical substituents are selected from the group consisting of: —X, —R$^{46}$, —O$^-$, =O, —OR$^{46}$, —SR$^{46}$, —S$^-$, =S, =NR$^{46}$R$^{47}$, =NR$^{46}$, —CX$_3$, —CF$_3$, —CN, —OCN, —SCN, —NO, —NO$_2$, =N$_2$, —N$_3$, —S(O)$_2$O$^-$, —S(O)$_2$OH, —S(O)$_2$R$^{46}$, —OS(O$_2$)O$^-$, —OS(O)$_2$R$^{46}$, —P(O)(O$^-$)$_2$, —P(O)(OR$^{46}$)(O$^-$), —OP(O)(OR$^{46}$)(OR$^{47}$), —C(O)R$^{46}$, —C(S)R$^{46}$, —C(O)OR$^{46}$, —C(O)NR$^{46}$R$^{47}$, —C(O)O$^-$, —C(S)OR$^{46}$, —NR$^{48}$C(O)NR$^{46}$R$^{47}$, —NR$^{48}$C(S)NR$^{46}$R$^{47}$, —NR$^{49}$C(NR$^{48}$)NR$^{46}$R$^{47}$ and —C(NR$^{48}$)NR$^{46}$R$^{47}$, where each X is independently a halogen; each R$^{46}$, R$^{47}$, R$^{48}$ and R$^{49}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl, substituted heteroarylalkyl, —NR$^{50}$R$^{51}$, —C(O)R$^{50}$ or —S(O)$_2$R$^{50}$ or optionally R$^{50}$ and R$^{51}$ together with the atom to which they are both attached form a cycloheteroalkyl or substituted cycloheteroalkyl ring; and $R^{50}$ and $R^{51}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl or substituted heteroarylalkyl. In a particular embodiment, substituted groups are substituted with one or more substituents, particularly with 1 to 3 substituents, and in particular with one substituent group. In a further particular embodiment the substituent group or groups are selected from halo, cyano, nitro, trifluoromethyl, trifluoromethoxy, azido, —NR'''SO$_2$R'', —SO$_2$NR''R''', —C(O)R'', —C(O)OR'', —OC(O)R'', —NR'''C(O)R'', —C(O)NR''R''', —NR''R''', or —(CR'''R'''')$_t$OR'''; wherein each R'' is independently selected from H, $C_1$-$C_8$ alkyl, —(CH$_2$)$_t$(C$_6$-C$_{10}$ aryl), —(CH$_2$)$_t$(C$_5$-C$_{10}$ heteroaryl), —(CH$_2$)$_t$(C$_3$-C$_{10}$ cycloalkyl), and —(CH$_2$)$_t$(C$_5$-C$_{10}$ heterocycloalkyl), wherein t is an integer from 0 to 4 and any aryl, heteroaryl, cycloalkyl or heterocycloalkyl groups present, may themselves be substituted by $C_1$-$C_4$ alkyl, halo, $C_1$-$C_4$ alkoxy, $C_{1-4}$ haloalkyl, $C_1$-$C_4$ hydroxyalkyl, or $C_1$-$C_4$ haloalkoxy or hydroxy. Each of R''' and R'''' independently represents H or $C_1$-$C_6$ alkyl.

Examples of representative substituted aryls include the following

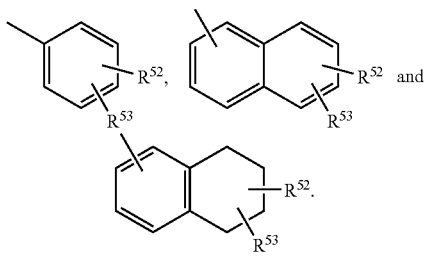

In these formulae one of $R^{52}$ and $R^{53}$ may be hydrogen and at least one of $R^{52}$ and $R^{53}$ is each independently selected from alkyl, alkenyl, alkynyl, cycloheteroalkyl, alkanoyl, alkoxy, aryloxy, heteroaryloxy, alkylamino, arylamino, heteroarylamino, NR$^{54}$COR$^{55}$, NR$^{54}$SOR$^{55}$, NR$^{54}$SO$_2$R$^{57}$, COOalkyl, COOaryl, CONR$^{54}$R$^{55}$, CONR$^{54}$OR$^{55}$, NR$^{54}$R$^{55}$, SO$_2$NR$^{54}$R$^{55}$, S-alkyl, S-alkyl, SOalkyl, SO$_2$alkyl, Saryl, SOaryl, SO$_2$aryl; or $R^{52}$ and $R^{53}$ may be joined to form a cyclic ring (saturated or unsaturated) from 5 to 8 atoms, optionally containing one or more heteroatoms selected from the group N, O or S. $R^{54}$, $R^{55}$, and $R^{56}$ are independently hydrogen, alkyl, alkenyl, alkynyl, perfluoroalkyl, cycloalkyl, cycloheteroalkyl, aryl, substituted aryl, heteroaryl, substituted or hetero alkyl or the like.

'Hetero' when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. cycloheteroalkyl, aryl, e.g. heteroaryl, cycloalkenyl, cycloheteroalkenyl, and the like having from 1 to 5, and especially from 1 to 3 heteroatoms.

'Heteroaryl' means an aromatic ring structure, mono-cyclic or polycyclic, that includes one or more heteroatoms and 5 to 12 ring members, more usually 5 to 10 ring members. The heteroaryl group can be, for example, a five membered or six membered monocyclic ring or a bicyclic structure formed from fused five and six membered rings or two fused six membered rings or, by way of a further example, two fused five membered rings. Each ring may contain up to about four heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five. Examples of five membered monocyclic heteroaryl groups include but are not limited to pyrrole, furan, thiophene, imidazole, furazan, oxazole, oxadiazole, oxatriazole, isoxazole, thiazole, isothiazole, pyrazole, triazole and tetrazole groups. Examples of six membered monocyclic heteroaryl groups include but are not limited to pyridine, pyrazine, pyridazine, pyrimidine and triazine. Particular examples of bicyclic heteroaryl groups containing a five membered ring fused to another five membered ring include but are not limited to imidazothiazole and imidazoimidazole. Particular examples of bicyclic heteroaryl groups containing a six membered ring fused to a five membered ring include but are not limited to benzfuran, benzthiophene, benzimidazole, benzoxazole, isobenzoxazole, benzisoxazole, benzthiazole, benzisothiazole, isobenzofuran, indole, isoindole, isoindolone, indolizine, indoline, isoindoline, purine (e.g., adenine, guanine), indazole, pyrazolopyrimidine, triazolopyrimidine, benzodioxole and pyrazolopyridine groups. Particular examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups. Particular heteroaryl groups are those derived from thiophene, pyrrole, benzothiophene, benzofuran, indole, pyridine, quinoline, imidazole, oxazole and pyrazine.

Examples of representative heteroaryls include the following:

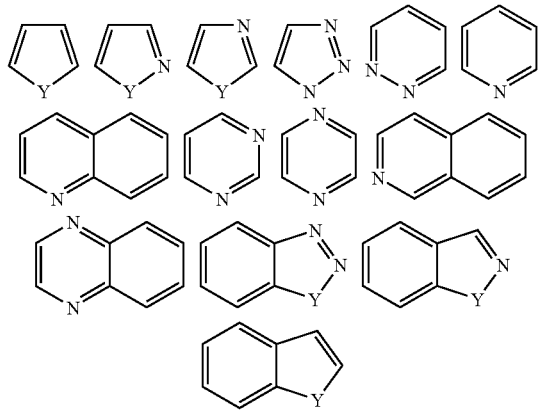

wherein each Y is selected from carbonyl, N, NR$^{58}$, O and S; and $R^{58}$ is independently hydrogen, alkyl, cycloalkyl, cycloheteroalkyl, aryl, heteroaryl and heteroalkyl. The term 'heteroaryl' includes 'bicycloheteroaryl' as defined below.

'Bicycloheteroaryl' refers to a monovalent bicycloheteroaromatic group which may result from the removal of one hydrogen atom from a single atom of a parent bicycloheteroaromatic ring system. A bicycloheteroaryl group may have a structure that may consist of two unsaturated or aromatic rings; one unsaturated or aromatic ring and one fully saturated ring; or one unsaturated or aromatic ring and one partially saturated ring. In particular, a bicycloheteroaryl group comprises from 9 to 14 atoms. Representative bicycloheteroaryl groups may include, but are not limited to, groups derived from benzofuran, benzimidazole, benzindazole, benzdioxane, chromene, chromane, cinnoline, phthalazine, indole, indoline, indolizine, isobenzofuran, isochromene, isoindole, isoindoline, isoquinoline, benzothiazole, benzoxazole, naphthyridine, benzoxadiazole, pteridine, purine, benzopyran, benzpyrazine, pyridopyrimidine, quinazoline, quinoline, quinolizine, quinoxaline, benzomorphan, tetrahydroisoquinoline, tetrahydroquinoline, and the like. Exemplary bicycloheteroaryl groups include, benzothiophene, benzofuran, benzothiazole, indole, quinoline, isoquinoline, benzimidazole, benzoxazole and benzdioxane.

As used herein, the term 'heterocycloalkyl' refers to a 4-7 membered, stable heterocyclic non-aromatic ring and fused rings containing one or more heteroatoms independently selected from N, O and S. A fused heterocyclic ring system may include carbocyclic rings and need only include one heterocyclic ring. Examples of heterocyclic rings include, but are not limited to, morpholine, piperidine (e.g. 1-piperidinyl, 2-piperidinyl, 3-piperidinyl and 4-piperidinyl), pyrrolidine (e.g. 1-pyrrolidinyl, 2-pyrrolidinyl and 3-pyrrolidinyl), pyrrolidone, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazine, and N-alkyl piperazines such as N-methyl piperazine. Further examples include thiomorpholine and its S-oxide and S,S-dioxide (particularly thiomorpholine). Still further examples include azetidine, piperidone, piperazone, and N-alkyl piperidines such as N-methyl piperidine. Particular examples of heterocycloalkyl groups are shown in the following illustrative examples:

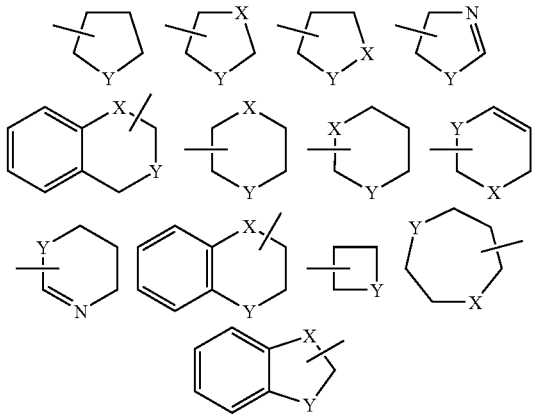

wherein each X is selected from $CR^{58}$, $CR^{58}_2$, $NR^{58}$, O and S; and each Y is selected from $NR^{58}$, O and S; and $R^{58}$ is independently hydrogen, alkyl, cycloalkyl, heterocycloalkyl, aryl, heteroaryl, heteroalkyl or the like. These heterocycloalkyl rings may be optionally substituted with one or more groups selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—. Substituting groups include carbonyl or thiocarbonyl which provide, for example, lactam and urea derivatives. The term 'heterocycloalkyl' includes 'heterocycloalkenyl' as defined below.

Examples of representative heterocycloalkenyls include the following:

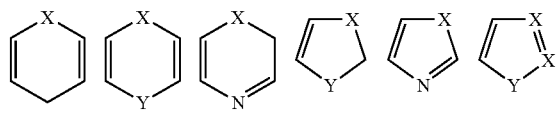

wherein each X is selected from $CR^{58}$, $CR^{58}_2$, $NR^{58}$, O and S; and each Y is selected from carbonyl, N, $NR^{58}$, O and S; and $R^{58}$ is independently hydrogen, alkyl, cycloalkyl, cycloheteroalkyl, aryl, heteroaryl, heteroalkyl or the like.

Examples of representative aryl having hetero atoms containing substitution include the following:

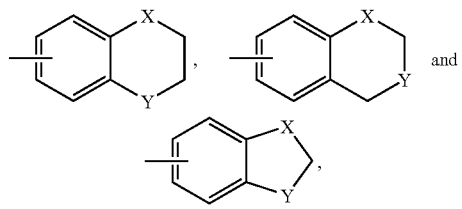

wherein each X is selected from $CR^{58}_2$, $NR^{58}$, O and S; and each Y is selected from carbonyl, $NR^{58}$, O and S; and $R^{58}$ is independently hydrogen, alkyl, cycloalkyl, cycloheteroalkyl, aryl, heteroaryl, heteroalkyl or the like.

'Hetero substituent' refers to a halo, O, S or N atom-containing functionality that may be present as an 'R' in a 'R'C group present as substituents directly on a variable ring atom of the compounds of this invention or may be present as a substituent in the 'substituted' aryl and aliphatic groups present in the compounds. Examples of hetero substituents include:
-halo,
—NO$_2$, —NH$_2$, —NHR$^{59}$, —N(R$^{59}$)$_2$,
—NRCOR, —NR$^{59}$SOR$^{59}$, —NR$^{59}$SO$_2$R$^{59}$, OH, CN,
—CO$_2$H,
—R$^{59}$—OH, —O—R$^{59}$, —COOR$^{59}$,
—CON(R$^{59}$)$_2$, —CONROR$^{59}$,
—SO$_3$H, —R$^{59}$—S, —SO$_2$N(R$^{59}$)$_2$,
—S(O)R$^{59}$, —S(O)$_2$R$^{59}$
wherein each R$^{59}$ is independently an aryl or aliphatic, optionally with substitution. Among hetero substituents containing R$^{59}$ groups, preference is given to those materials having aryl and alkyl R$^{59}$ groups as defined herein. Preferred hetero substituents are those listed above.

'Hydrogen bond donor' group refers to a group containing O—H, N—H functionality. Examples of 'hydrogen bond donor' groups include —OH, —NH$_2$, and —NH—R$^{60}$, wherein R$^{60}$ is alkyl, cycloalkyl, aryl or heteroaryl.

'Dihydroxyphosphoryl' refers to the radical —PO(OH)$_2$.

'Substituted dihydroxyphosphoryl' refers to a dihydroxyphosphoryl group substituted with one or more of those groups recited in the definition of 'substituted' herein, and particularly refers to a dihydroxyphosphoryl radical wherein one or both of the hydroxyl groups are substituted.

'Aminohydroxyphosphoryl' refers to the radical —PO(OH)NH$_2$.

'Substituted aminohydroxyphosphoryl' refers to an aminohydroxyphosphoryl group substituted with one or more of those groups recited in the definition of 'substituted' herein, and particularly refers to an aminohydroxyphosphoryl wherein the amino group is substituted with one or two substituents. In certain embodiments, the hydroxyl group can also be substituted.

'Thioalkoxy' refers to the group —SR$^{61}$ where R$^{61}$ is alkyl.

'Substituted thioalkoxy' refers to a thioalkoxy group substituted with one or more of those groups recited in the definition of 'substituted' herein, and particularly refers to a thioalkoxy group having 1 or more substituents, for instance from 1 to 5 substituents, and particularly from 1 to 3 substituents.

'Sulfanyl' refers to the radical HS—.

'Substituted sulfanyl' refers to a sulfanyl group substituted with one or more of those groups recited in the definition of 'substituted' herein.

'Sulfonyl' refers to the divalent radical —S(O$_2$)—.

'Substituted sulfonyl' refers to a radical such as —(O$_2$)S—R$^{62}$, wherein R$^{62}$ is any substituent described herein. Exemplary 'substituted sulfonyl' groups include —SO$_2$—C$_1$-C$_8$ alkyl, —SO$_2$—(CH$_2$)$_t$(C$_6$-C$_{10}$ aryl), —SO$_2$—(CH$_2$)$_t$(C$_5$-C$_{10}$ heteroaryl), —SO$_2$—(CH$_2$)$_t$(C$_3$-C$_{10}$ cycloalkyl), and —SO$_2$—(CH$_2$)$_t$(C$_5$-C$_{10}$ heterocycloalkyl), wherein t is an integer from 0 to 4 and any aryl, heteroaryl, cycloalkyl or heterocycloalkyl groups present, may themselves be substituted by C$_1$-C$_4$ alkyl, halo, C$_1$-C$_4$ alkoxy, C$_1$-C$_4$ haloalkyl, C$_1$-C$_4$ hydroxyalkyl, or C$_1$-C$_4$ haloalkoxy or hydroxyl.

'Aminosulfonyl' or 'sulfonamide' refers to the radical —S(O$_2$)NH$_2$, and 'substituted aminosulfonyl' or 'substituted sulfonamide" refers to a radical such as —S(O$_2$)NR$^{63}$$_2$, wherein each R$^{63}$ is independently any substituent described herein. Exemplary 'substituted aminosulfonyl' or 'substituted sulfonamide' groups include as —S(O$_2$)N(R$^{63}$)—C$_1$-C$_8$ alkyl, —S(O$_2$)N(R$^{63}$)—(CH$_2$)$_t$(C$_6$-C$_{10}$ aryl), —S(O$_2$)N(R$^{63}$)—(CH$_2$)t(C$_5$-C$_{10}$ heteroaryl), —S(O$_2$)N(R$^{62}$)—(CH$_2$)$_t$(C$_3$-C$_{10}$ cycloalkyl), and —S(O$_2$)N(R$^{63}$)—(CH$_2$)$_t$(C$_5$-C$_{10}$ heterocycloalkyl), wherein t is an integer from 0 to 4; each R$^{63}$ independently represents H or C$_1$-C$_6$ alkyl; and any aryl, heteroaryl, cycloalkyl or heterocycloalkyl groups present, may themselves be substituted by C$_1$-C$_4$ alkyl, halo, C$_1$-C$_4$ alkoxy, C$_1$-C$_4$ haloalkyl, C$_1$-C$_4$ hydroxyalkyl, or C$_1$-C$_4$ haloalkoxy or hydroxy. Each R$^{63}$ independently represents H or C$_1$-C$_6$ alkyl.

'Sulfone' refers to the group —SO$_2$R$^{64}$. In particular embodiments, R$^{64}$ is selected from H, lower alkyl, alkyl, aryl and heteroaryl.

'Sulfo' or 'sulfonic acid' refers to a radical such as —SO$_3$H.

'Substituted sulfo' or 'sulfonic acid ester' refers to a radical such as —SO$_3$R$^{65}$, wherein R$^{65}$ is substituted or unsubstituted alkyl or substituted or unsubstituted aryl. Exemplary 'substituted sulfo' or 'sulfonic acid ester' groups include SO$_3$—C$_1$-C$_8$ alkyl, SO$_3$—(CH$_2$)$_t$(C$_6$-C$_{10}$ aryl), SO$_3$—(CH$_2$)$_t$(C$_5$-C$_{10}$ heteroaryl), SO$_3$—(CH$_2$)$_t$(C$_3$-C$_{10}$ cycloalkyl), and SO$_3$—(CH$_2$)$_t$(C$_5$-C$_{10}$ heterocycloalkyl), wherein t is an integer from 0 to 4 and any aryl, heteroaryl, cycloalkyl or heterocycloalkyl groups present, may themselves be substituted by C$_1$-C$_4$ alkyl, halo, C$_1$-C$_4$ alkoxy, C$_1$-C$_4$ haloalkyl, C$_1$-C$_4$ hydroxyalkyl, or C$_1$-C$_4$ haloalkoxy or hydroxy.

'Sulfinyl' refers to the divalent radical —S(O)—. 'Substituted sulfinyl' refers to a radical such as —SOR$^{66}$, wherein R$^{66}$ is any substituent described herein. Exemplary 'substituted sulfinyl' groups include SO—C$_1$-C$_8$ alkyl, SO—(CH$_2$)$_t$(C$_6$-C$_{10}$ aryl), SO—(CH$_2$)$_t$(C$_5$-C$_{10}$ heteroaryl), SO—(CH$_2$)$_t$(C—C$_{10}$ cycloalkyl), and SO—(CH$_2$)$_t$(C$_5$-C$_{10}$ heterocycloalkyl), wherein t is an integer from 0 to 4 and any aryl, heteroaryl, cycloalkyl or heterocycloalkyl groups present, may themselves be substituted by C$_1$-C$_4$ alkyl, halo, C$_1$-C$_4$ alkoxy, C$_1$-C$_4$ haloalkyl, C$_1$-C$_4$ hydroxyalkyl, or C$_1$-C$_4$ haloalkoxy or hydroxy.

'Sulfonamide' refers to a group of compounds containing the chemical group —SO$_2$NH$_2$.

'Thioaryloxy' refers to the group —SR$^{67}$, where R$^{67}$ is aryl.

'Thioketo' refers to the group =S.

'Thiol' refers to the group —SH.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

'Pharmaceutically acceptable' means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

'Pharmaceutically acceptable salt' refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term "pharmaceutically acceptable cation" refers to an acceptable cationic counter-ion of an acidic functional group. Such cations are exemplified by sodium, potassium, calcium, magnesium, ammonium, tetraalkylammonium cations, and the like.

'Pharmaceutically acceptable vehicle' refers to a diluent, adjuvant, excipient or carrier with which a compound of the invention is administered.

'Preventing' or 'prevention' refers to a reduction in risk of acquiring a disease or disorder (i.e., causing at least one of the clinical symptoms of the disease not to develop in a subject that may be exposed to or predisposed to the disease but does not yet experience or display symptoms of the disease). This term encompasses the term 'prophylaxis', which means a measure taken for the prevention of a disease.

'Prodrugs' refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

'Solvate' refers to forms of the compound that are associated with a solvent, usually by a solvolysis reaction. This physical association includes hydrogen bonding. Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. 'Solvate' encompasses both solution-phase and isolable solvates. Representative solvates include hydrates, ethanolates and methanolates.

'Subject' includes humans. The terms 'human', 'patient' and 'subject' are used interchangeably herein.

'Therapeutically effective amount' means the amount of a compound that, when administered to a subject for treating a disease, is sufficient to effect such treatment for the disease. The 'therapeutically effective amount' can vary depending on the compound, the disease and its severity, and the age, weight, etc., of the subject to be treated.

'Treating' or 'treatment' of any disease or disorder refers, in one embodiment, to ameliorating the disease or disorder (i.e., arresting or reducing the development of the disease or at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or disorder, either physically, (e.g., stabilization of a discernible symptom), physiologically, (e.g., stabilization of a physical parameter), or both. In yet another embodiment, 'treating' or 'treatment' refers to delaying the onset of the disease or disorder.

'Compounds of the present invention', and equivalent expressions, are meant to embrace compounds of the Formula (e) as hereinbefore described, which expression includes the prodrugs, the pharmaceutically acceptable salts, and the solvates, e.g., hydrates, where the context so permits. Similarly, reference to intermediates, whether or not they themselves are claimed, is meant to embrace their salts, and solvates, where the context so permits.

Other derivatives of the compounds of this invention have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendent on the compounds of this invention are particularly useful prodrugs. In some cases it is desirable to prepare double ester type prodrugs such as (acyloxy)alkyl esters or ((alkoxycarbonyl)oxy)alkylesters. Particular such prodrugs are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

As used herein, the term 'isotopic variant' refers to a compound that contains unnatural proportions of isotopes at one or more of the atoms that constitute such compound. For example, an 'isotopic variant' of a compound can contain one or more non-radioactive isotopes, such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art. Likewise, the invention may include the preparation of isotopic variants with radio-isotopes, in the instance for example, where the resulting compounds may be used for drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Further, compounds may be prepared that are substituted with positron emitting isotopes, such as $^{11}$C, $^{18}$F, $^{15}$O and $^{13}$N, and would be useful in Positron Emission Topography (PET) studies for examining substrate receptor occupancy.

All isotopic variants of the compounds provided herein, radioactive or not, are intended to be encompassed within the scope of the invention.

It is also to be understood that compounds that have the same molecular formula but differ in the nature or sequence of bonding of their atoms or the arrangement of their atoms in space are termed 'isomers'. Isomers that differ in the arrangement of their atoms in space are termed 'stereoisomers'.

Stereoisomers that are not mirror images of one another are termed 'diastereomers' and those that are non-superimposable mirror images of each other are termed 'enantiomers'. When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a 'racemic mixture'.

'Tautomers' refer to compounds that are interchangeable forms of a particular compound structure, and that vary in the displacement of hydrogen atoms and electrons. Thus, two structures may be in equilibrium through the movement of it electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

The compounds of this invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

The Compounds

As described herein, the present invention relates to the identification of compounds that modulate the activity of the thyroid hormone receptor.

In another aspect of the present invention, compounds have been identified that are capable of use in diagnostic and therapeutic methods, including screening for derivatives that demonstrate thyroid hormone receptor modulatory activity, and that may be administered to treat or inhibit the occurrence of hyperthyroidism or thyrotoxicosis.

In one embodiment of the invention, compounds are disclosed that are TR modulators, having a formula selected from:

In one particular embodiment of the invention, with respect to formula I, m is 1.

In one particular embodiment of the invention, with respect to formula I, $R^3$ is alkyl, nitro, alkoxy, halo or haloalkyl.

In one particular embodiment of the invention, with respect to formula I, $R^3$ is nitro.

In one particular embodiment of the invention, with respect to formula I, $R^3$ is haloalkyl.

In one particular embodiment of the invention, with respect to formula I, $R^3$ is trifluoromethyl.

In one particular embodiment of the invention, with respect to formula I, $R^3$ is $NHSO_2Me$.

In one particular embodiment of the invention, with respect to formula I, m' is 1.

In one particular embodiment of the invention, with respect to formula I, $R^4$ is alkyl, alkoxy, halo or haloalkyl and m' is 1.

In one particular embodiment of the invention, with respect to formula I, $R^4$ is $CF_3$, OMe, F, or Cl; and m' is 1.

In one particular embodiment of the invention, with respect to formula I, m' is 2.

In one particular embodiment of the invention, with respect to formula I, each $R^4$ is independently alkyl, alkoxy, halo or haloalkyl and m' is 2.

In one particular embodiment of the invention, with respect to formula I, each $R^4$ is independently Me, iso-Pr, $CF_3$, OMe, F, or Cl; and m' is 2.

In one embodiment of the invention, compounds are disclosed that are TR modulators, having a formula selected from:

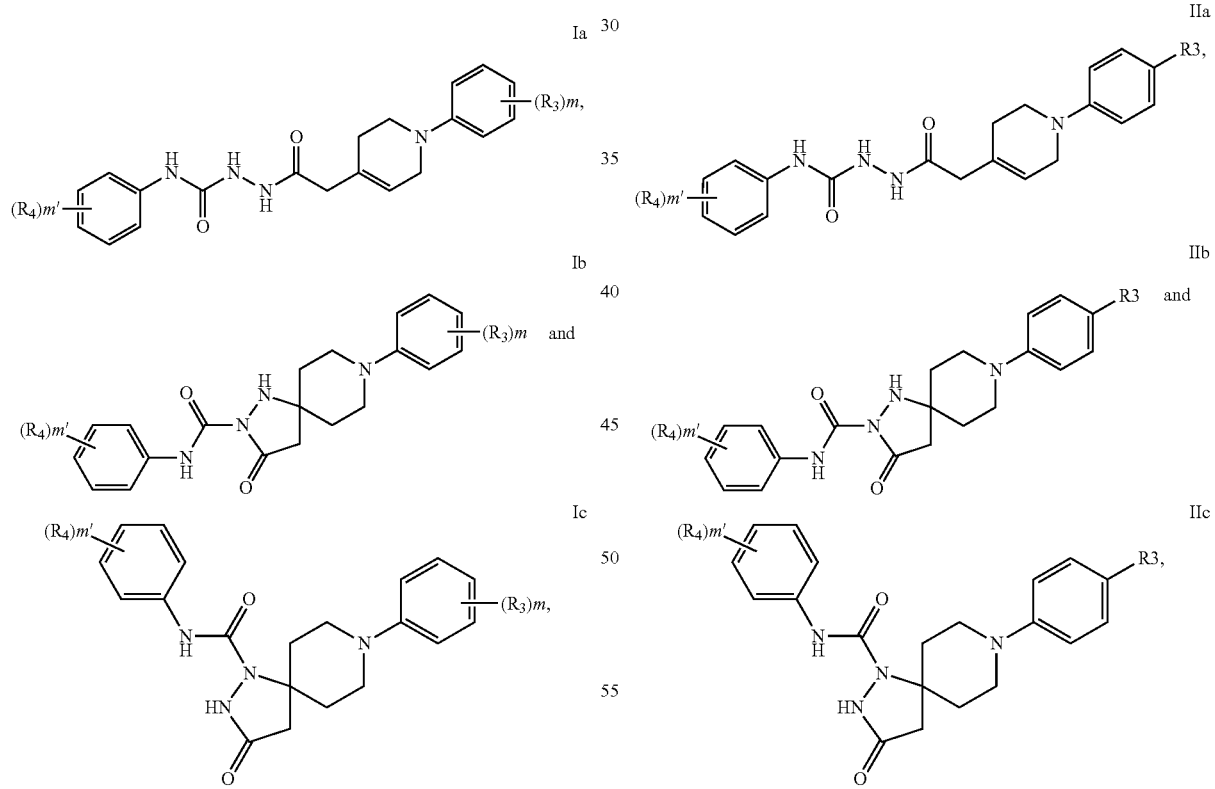

or a pharmaceutically acceptable salt, solvate or prodrug thereof, and stereoisomers, tautomers and isotopic variants thereof; and wherein:
each of $R^3$ and $R^4$ are independently H, substituted or unsubstituted alkyl, substituted or unsubstituted alkoxy, substituted or unsubstituted amino, substituted or unsubstituted amido, $NHSO_2$-alkyl, halo, or nitro; and each of m and m' are independently selected from 0-4.

or a pharmaceutically acceptable salt, solvate or prodrug thereof, and stereoisomers, tautomers and isotopic variants thereof; and wherein:
each of $R^3$ and $R^4$ are independently H, substituted or unsubstituted alkyl, substituted or unsubstituted alkoxy, substituted or unsubstituted amino, substituted or unsubstituted amido, $NHSO_2$-alkyl, halo, or nitro; and m' is selected from 0-4.

In one particular embodiment of the invention, with respect to formula II, $R^3$ is alkyl, nitro, alkoxy, halo or haloalkyl.

In one particular embodiment of the invention, with respect to formula II, $R^3$ is nitro.

In one particular embodiment of the invention, with respect to formula II, $R^3$ is haloalkyl.

In one particular embodiment of the invention, with respect to formula II, $R^3$ is trifluoromethyl.

In one particular embodiment of the invention, with respect to formula II, $R^3$ is $NHSO_2Me$.

In one particular embodiment of the invention, with respect to formula II, m' is 1.

In one particular embodiment of the invention, with respect to formula II, $R^4$ is alkyl, alkoxy, halo or haloalkyl and m' is 1.

In one particular embodiment of the invention, with respect to formula II, $R^4$ is $CF_3$, OMe, F, or Cl; and m' is 1.

In one particular embodiment of the invention, with respect to formula II, m' is 2.

In one particular embodiment of the invention, with respect to formula II, each $R^4$ is independently alkyl, alkoxy, halo or haloalkyl and m' is 2.

In one particular embodiment of the invention, with respect to formula II, each $R^4$ is independently Me, iso-Pr, $CF_3$, OMe, F, or Cl; and m' is 2.

In one embodiment of the invention, compounds are disclosed that are TR modulators, having a formula selected from:

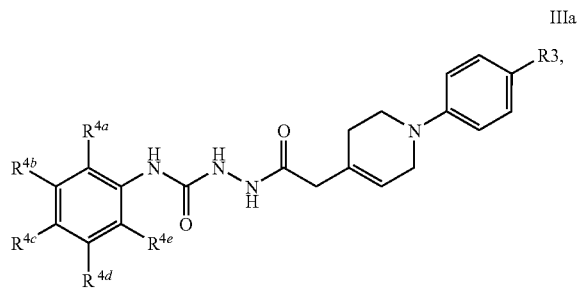

IIIa

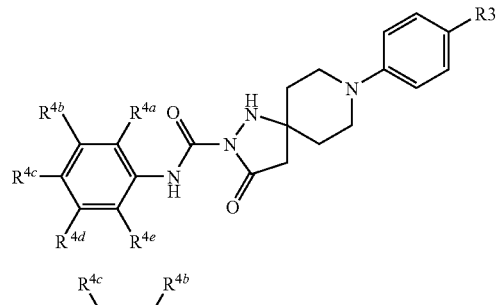

IIIb

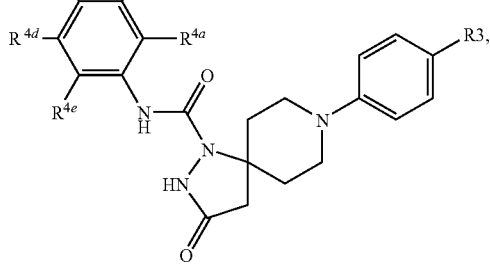

IIIc or a pharmaceutically acceptable salt, solvate or prodrug thereof, and stereoisomers, tautomers and isotopic variants thereof; and wherein:

each of $R^3$ and $R^{4a-e}$ are independently H, substituted or unsubstituted alkyl, substituted or unsubstituted alkoxy, substituted or unsubstituted amino, substituted or unsubstituted amido, $NHSO_2$-alkyl, halo, or nitro.

In one particular embodiment of the invention, with respect to formula III, $R^3$ is alkyl, nitro, alkoxy, halo or haloalkyl.

In one particular embodiment of the invention, with respect to formula III, $R^3$ is nitro In one particular embodiment of the invention, with respect to formula III, $R^3$ is haloalkyl.

In one particular embodiment of the invention, with respect to formula III, $R^3$ is trifluoromethyl.

In one particular embodiment of the invention, with respect to formula III, $R^3$ is $NHSO_2Me$.

In one particular embodiment of the invention, with respect to formula III, $R^{4a}$ is Me, Et, iso-Pr, F, or OMe.

In one particular embodiment of the invention, with respect to formula III, $R^{4b}$ is Me, Et, iso-Pr, F, or OMe.

In one particular embodiment of the invention, with respect to formula III, $R^{4c}$ is Me, Et, iso-Pr, F, or OMe.

In one particular embodiment of the invention, with respect to formula III, $R^{4e}$ is Me, Et, iso-Pr, F, or OMe.

In one particular embodiment of the invention, with respect to formula III, $R^{4a}$ is iso-Pr and $R^{4e}$ is Me.

In one particular embodiment of the invention, with respect to formula III, $R^{4b}$ is Me and $R^{4e}$ is OMe.

In one particular embodiment of the invention, with respect to formula III, each of $R^{4b}$ and $R^{4c}$ is F.

In one particular embodiment of the invention, with respect to formula III, each of $R^{4a}$, $R^{4c}$ and $R^{4e}$ is F.

In one embodiment of the invention, quinoline compounds are disclosed that are TR modulators, having a formula selected from:

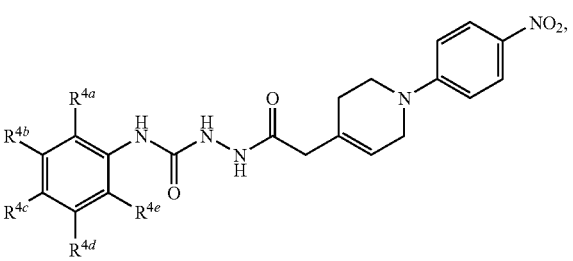

IVa

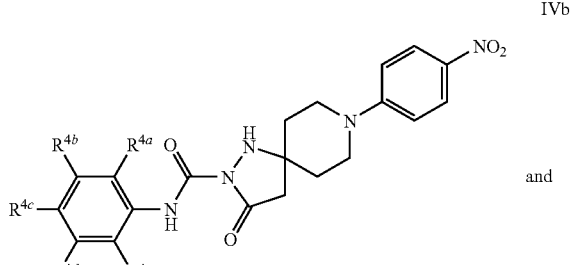

IVb and

IVc

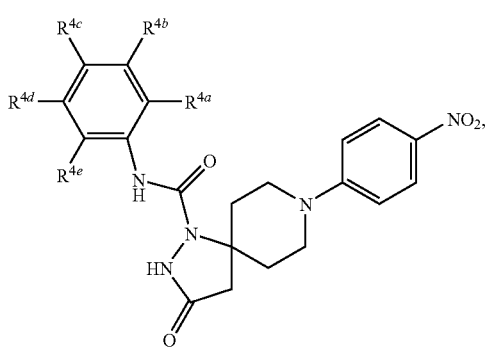

or a pharmaceutically acceptable salt, solvate or prodrug thereof, and stereoisomers, tautomers and isotopic variants thereof; and wherein:

each of $R^{4a-e}$ are independently H, substituted or unsubstituted alkyl, substituted or unsubstituted alkoxy, substituted or unsubstituted amino, substituted or unsubstituted amido, NHSO$_2$-alkyl, halo, or nitro.

In one particular embodiment of the invention, with respect to formula IV, $R^{4a}$ is Me, Et, iso-Pr, F, or OMe.

In one particular embodiment of the invention, with respect to formula N, $R^{4b}$ is Me, Et, iso-Pr, F, or OMe.

In one particular embodiment of the invention, with respect to formula IV, $R^{4c}$ is Me, Et, iso-Pr, F, or OMe.

In one particular embodiment of the invention, with respect to formula IV, $R^{4c}$ is Me, Et, iso-Pr, F, or OMe.

In one particular embodiment of the invention, with respect to formula IV, $R^{4a}$ is iso-Pr and $R^{4e}$ is Me.

In one particular embodiment of the invention, with respect to formula IV, $R^{4b}$ is Me and $R^{4e}$ is OMe.

In one particular embodiment of the invention, with respect to formula N, each of $R^{4b}$ and $R^{4c}$ is F.

In one particular embodiment of the invention, with respect to formula N, each of $R^{4a}$, $R^{4c}$ and $R^{4e}$ is F.

In one embodiment of the invention, compounds are disclosed that are TR modulators, having a formula selected from:

Va

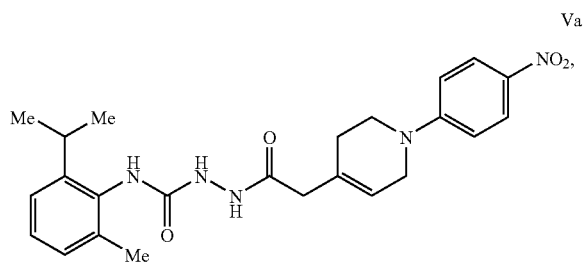

Vb

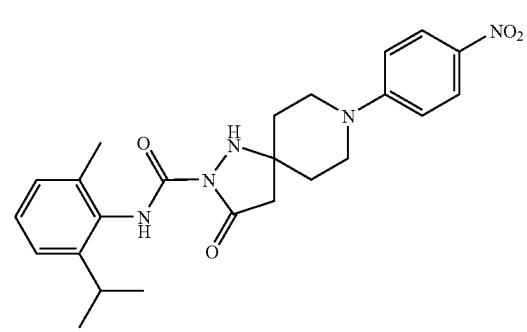

and

Vc

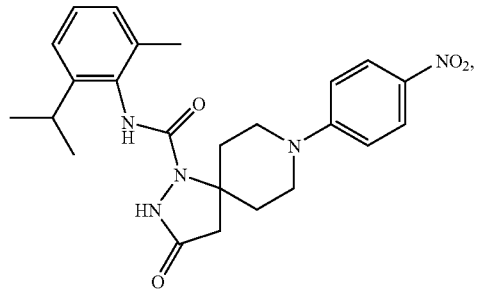

or a pharmaceutically acceptable salt, solvate or prodrug thereof, and stereoisomers, tautomers and isotopic variants thereof.

In certain embodiments, when R as defined herein is alkyl; the alkyl group is $C_1$-$C_8$alkyl. In another embodiment, the alkyl group is $C_1$-$C_6$alkyl. In a further embodiment, the alkyl group is $C_1$-$C_4$alkyl.

In one embodiment, the alkyl group is optionally substituted by one or more groups (such as 1 to 3 substituents, in particular one substituent group, which substituent group may be independently selected from halo, hydroxy, cyano, nitro, trifluoromethyl, trifluoromethoxy, azido, —NR$^{10}$SO$_2$R$^9$, —SO$_2$NR$^9$R$^{10}$, —C(O)R$^9$, —C(O)OR$^9$, —OC(O)R$^9$, —NR$^{10}$C(O)R$^9$, —C(O)NR$^9$R$^{10}$, —NR$^9$R$^{10}$, —(CR$^{10}$R$^{11}$)$_m$OR$^{10}$ and wherein m is an integer from 1 to 5.

In one embodiment, the alkyl group is optionally substituted by one or more halogens.

In one embodiment, the alkyl group is optionally substituted by one or more F.

In one embodiment, the alkyl group is optionally substituted by OH.

In one embodiment, each $R^9$ is independently selected from H, $C_1$-$C_8$alkyl, —(CH$_2$)$_t$(C$_6$-$C_{10}$ aryl), —(CH$_2$)$_t$(C$_5$-$C_{10}$ heteroaryl), —(CH$_2$)$_t$(C$_3$-$C_{10}$ cycloalkyl), and —(CH$_2$)$_t$(C$_5$-$C_{10}$ heterocycloalkyl), wherein t is an integer from 0 to 4.

In one embodiment, each $R^9$ is as described above, and any aryl, heteroaryl, cycloalkyl or heterocycloalkyl groups present, may themselves be substituted by $C_1$-$C_4$alkyl, halo, $C_1$-$C_4$alkoxy, $C_1$-$C_4$haloalkyl, $C_1$-$C_4$hydroxyalkyl, or $C_1$-$C_4$haloalkoxy or hydroxy.

In one embodiment, each $R^9$ is as described above, and each of $R^{10}$ and $R^{11}$ independently represents H or $C_1$-$C_6$alkyl.

In one embodiment, each $R^9$ is as described above and each of $R^{12}$ and $R^{13}$ independently represents H or $C_1$-$C_4$alkyl.

In one embodiment, each of $R^{10}$ and $R^{11}$ independently represents H or $C_1$-$C_6$alkyl.

In one embodiment, each $R^9$ is other than H.

In certain embodiments, when R as defined herein is alkoxy; the alkoxy group is —OR$^9$; and R$^9$ is as described in the above embodiments; provided that R$^9$ is other than H.

In certain aspects, the present invention provides prodrugs and derivatives of the compounds according to the formulae above. Prodrugs are derivatives of the compounds of the invention, which have metabolically cleavable groups and become by solvolysis or under physiological conditions the compounds of the invention, which are pharmaceutically active, in vivo. Such examples include, but are not limited to, choline ester derivatives and the like, N-alkylmorpholine esters and the like.

Other derivatives of the compounds of this invention have activity in both their acid and acid derivative forms, but the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy)alkyl esters or ((alkoxycarbonyl)oxy)alkylesters. Preferred are the $C_1$ to $C_8$ alkyl, $C_2$-$C_8$ alkenyl, aryl, $C_2$-$C_{12}$ substituted aryl, and $C_7$-$C_{12}$ arylalkyl esters of the compounds of the invention.

Pharmaceutical Compositions

When employed as pharmaceuticals, the compounds of this invention are typically administered in the form of a pharmaceutical composition. Such compositions can be prepared in a manner well known in the pharmaceutical art and comprise at least one active compound.

Generally, the compounds of this invention are administered in a pharmaceutically effective amount. The amount of the compound actually administered will typically be determined by a physician, in the light of the relevant circumstances, including the condition to be treated, the chosen route of administration, the actual compound-administered, the age, weight, and response of the individual patient, the severity of the patient's symptoms, and the like.

The pharmaceutical compositions of this invention can be administered by a variety of routes including oral, rectal, transdermal, subcutaneous, intravenous, intramuscular, and intranasal. Depending on the intended route of delivery, the compounds of this invention are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the furansulfonic acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such Compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

The compounds of this invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pa., which is incorporated herein by reference.

The compounds of this invention can also be administered in sustained release forms or from sustained release drug delivery systems. A description of representative sustained release materials can be found in *Remington's Pharmaceutical Sciences.*

The following formulation examples illustrate representative pharmaceutical compositions that may be prepared in accordance with this invention. The present invention, however, is not limited to the following pharmaceutical compositions.

Formulation 1

Tablets

A compound of the invention is admixed as a dry powder with a dry gelatin binder in an approximate 1:2 weight ratio. A minor amount of magnesium stearate is added as a lubricant. The mixture is formed into 240-270 mg tablets (80-90 mg of active compound per tablet) in a tablet press.

Formulation 2

Capsules

A compound of the invention is admixed as a dry powder with a starch diluent in an approximate 1:1 weight ratio. The mixture is filled into 250 mg capsules (125 mg of active compound per capsule).

Formulation 3

Liquid

A compound of the invention (125 mg) may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water may then added to produce a total volume of 5 mL.

Formulation 4

Tablets

A compound of the invention may be admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Formulation 5

Injection

A compound of the invention is dissolved or suspended in a buffered sterile saline injectable aqueous medium to a concentration of approximately 5 mg/mL.

Formulation 6

Topical

Stearyl alcohol (250 g) and a white petrolatum (250 g) are melted at about 75° C. and then a mixture of a compound of the invention (50 g) methylparaben (0.25 g), propylparaben (0.15 g), sodium lauryl sulfate (10 g), and propylene glycol (120 g) dissolved in water (about 370 g) is added and the resulting mixture is stirred until it congeals.

Methods of Treatment

The present compounds are used as therapeutic agents for the treatment of conditions in mammals that are causally related or attributable to aberrant activity of the thyroid gland, and particularly, the aberrant production of thyroid hormone. Accordingly, the compounds and pharmaceutical compositions of this invention find use as therapeutics for preventing and/or treating conditions such as hyperthyroidism and thyrotoxicosis, in mammals including humans.

As a further aspect of the invention there is provided the present compounds for use as a pharmaceutical especially in the treatment or prevention of the aforementioned conditions and diseases. Thus, and as stated earlier, the present invention includes within its scope, and extends to, the recited methods of treatment, as well as to the compounds for such methods, and for the preparation of medicaments useful for such methods.

The compounds, prodrugs, isomers and pharmaceutically acceptable salts of this invention can be administered in a wide variety of different dosage forms, i.e., they may be combined with various pharmaceutically acceptable inert carriers in any suitable form. Such carriers include solid diluents or fillers, sterile aqueous media and various non-toxic organic solvents. The pharmaceutical compositions can be formulated to contain a daily dose, or a convenient fraction of a daily dose, in a dosage unit, which may be a single tablet or a capsule or a convenient volume of a liquid.

Any suitable route of administration may be used in the present invention. It is usually preferred to administer the compounds, prodrugs, isomers and pharmaceutically acceptable salts of this invention orally for reasons of convenience; however, they may be administered, for example, percutaneously, or as suppositories for absorption by the rectum, as desired in a given instance. As described above, the administration may be carried out in single or multiple doses, as appropriate.

All of the usual types of pharmaceutical compositions may be used in the present invention, including tablets, lozenges, hard candies, chewable tablets, granules, powders, sprays, capsules, pills, microcapsules, solutions, parenteral solutions, troches, injections (e.g., intravenous, intraperitoneal, intramuscular or subcutaneous), suppositories, elixirs, syrups and suspensions.

For parenteral administration, the compounds, prodrugs, isomers and pharmaceutically acceptable salts of this invention may be used as solutions in sesame or peanut oil, or as aqueous solutions (e.g., aqueous propyleneglycol), as the case may be, and they are best used in the form of a sterile aqueous solution which may contain other substances; for example, enough salts or glucose to make the solution isotonic, the pH of the solution being suitably adjusted and buffered, where necessary, and surfactants such as, for example, hydroxypropylcellulose. Such oily solutions are suitable for intra-articular, intramuscular and subcutaneous injection purposes. Such aqueous solutions are suitable for intravenous injection purposes.

The compounds, prodrugs, isomers and pharmaceutically acceptable salts of this invention may also be administered topically and this may be done by way of, e.g., creams, jellies, salves, lotions, gels, pastes, ointments, and the like, in accordance with standard pharmaceutical practice. The compounds, prodrugs, isomers and pharmaceutically acceptable salts of this invention of the present invention may also be administered transdermally (e.g., through the use of a patch). Any suitable formulation for transdermal application comprising a compound of the present invention may be employed and such formulations would generally also contain a suitable transdermal carrier, e.g., an absorbable pharmacologically acceptable solvent to promote and assist passage of the compounds through the subject's skin. For example, suitable transdermal devices may comprise the form of a bandage having a backing member and a reservoir containing the subject compound. Such bandage-type transdermal devices may further include suitable carriers, rate-controlling barriers, and means for securing the transdermal device to the subject's skin.

The compounds of this invention can be administered as the sole active agent or they can be administered in combination with other agents, including other compounds that demonstrate the same or a similar therapeutic activity, and that are determined to safe and efficacious for such combined administration.

General Synthetic Procedures

The bicycloheteroaryl compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The following proposed schemes are presented with details as to the preparation of representative compounds that have been listed hereinabove. The compounds of the invention may be prepared from known or commercially available starting materials and reagents by one skilled in the art of organic synthesis.

More particularly, the scheme relevant to the preparation of compounds derived from formulae Ia, IIa, IIIa, IVa and Va, is Scheme 1a, below.

Representative Synthesis

Scheme 2A

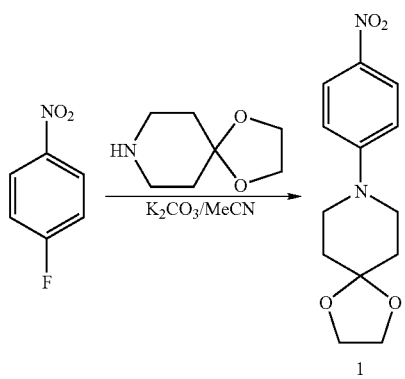

To 25 mL of acetonitrile (MeCN) was added $K_2CO_3$ (5.53 g, 40 mmol), 1,4-dioxa-8-azaspiro[4,5]decane (5.72 g, 40 mmol) and 1-fluoro-4-nitrobenzene (2.82 g, 20 mmol). The suspension was heated at reflux for 72 h under an argon atmosphere. The reaction mixture was diluted with $H_2O$ (100 mL) and was extracted with methylene chloride (4×250 mL). The organic layers were washed with brine and dried with Scheme 1a

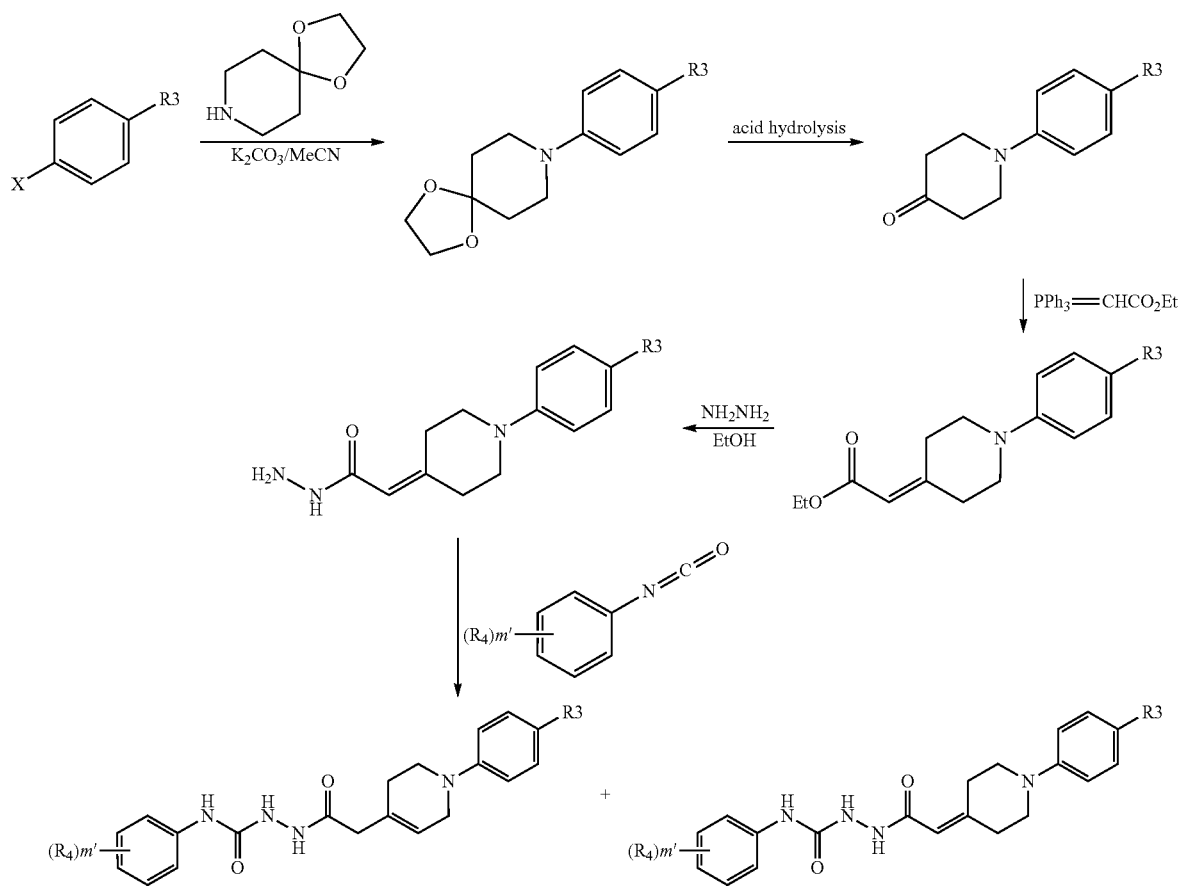

sodium sulfate. The solution was concentrated and precipitated out with cold diethyl ether to afford 1 (4.9 g, 93%). $^1$H NMR (400 MHz, CDCl$_3$): δ 1.81 (t, 4H), 3.58 (t, 4H), 4.02 (s, 4H), 6.83 (d, 2H), 8.12 (d, 2H).

Scheme 3a

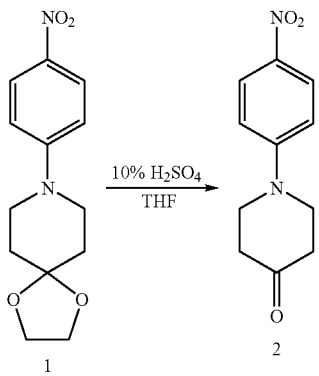

To a solution of tetrahydrofuran (40 mL) containing 10% H$_2$SO$_4$ (20 mL) was added 1 (3.4 g, 12.9 mmol). The reaction mixture was stirred vigorously for 4 days at room temperature, diluted with 60 mL H$_2$O and extracted with methylene chloride (4×250 mL). The solvent was evaporated and the product dried under vacuum to afford 2 (2.58 g, 91%). $^1$H NMR (400 MHz, CDCl$_3$): δ 2.63 (t, 4H), 3.82 (t, 4H), 6.86 (d, 2H), 8.18 (d, 2H).

Scheme 4a

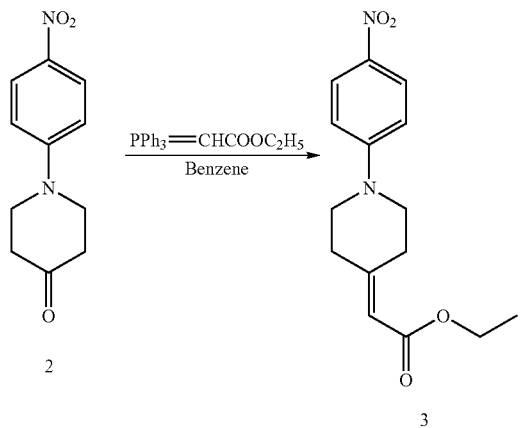

To anhydrous benzene (50 mL) was added 2 (1.32 g, 6 mmol) and Ph3P=CHCOOC2H5 (4.18 g, 12 mmol). The reaction mixture was heated at reflux for 24 hours under an argon atmosphere. The reaction was cooled and the solvent removed under vacuum. The crude mixture was dissolved in ethyl acetate, concentrated, and chromatographed on silica gel using hexanes/ethyl acetate (8:3) to afford compound 3 (1.42 g, 82%). The desired product is the first compound to be eluted from the column R$_f$~0.7).

$^1$H NMR (400 MHz, CDCl$_3$): δ 1.29 (t, 3H), 2.5 (d, 2H), 3.13 (t, 2H), 3.58 (m, 4H), 4.20 (q, 2H), 5.81 (s, 1H), 6.79 (d, 2H), 8.13 (d, 2H). MALDI-TOF: 289, calcd 289.13.

Scheme 5a

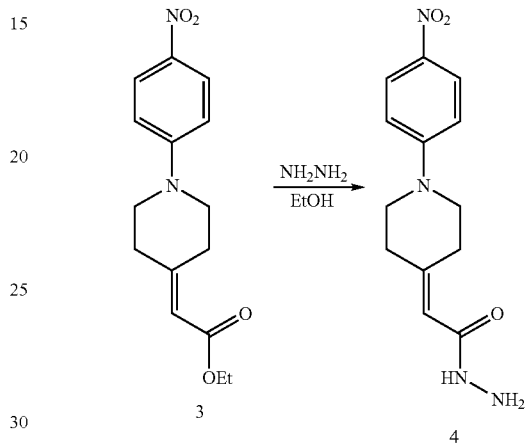

The mixture of 0.29 g of 3 (1 mMol) and 0.48 g anhydrous NH$_2$NH$_2$ (15 mMol) in 40 ml absolute ethanol was refluxed for 3 hours. After cooling to ambient temperature, the solution was concentrated in vacuo. The solid residue was crystallized from ethanol, affording compound 2.52 g (91%) of 4.
$^1$H NMR (DMSO) δ 2.22 (broad, 2H), 2.83 (broad, 2H), 3.60 (broad, 2H), 3.91 (broad, 2H), 5.68 (singlet, 1H), 7.02 (doublet, 2H), 8.05 (doublet, 2H)

In the final step, 0.5 mMol of the commercially available phenylisocyanate derivative is added to a solution of 4 (0.13 g, 0.5 mmol) in 1 ml dry CH$_2$Cl$_2$, and stirred at room temperature for 2 hours. The final product is separated by filtration and can be purified using various methods known to those skilled in the art.

The compounds corresponding to formulae Ib-Vb and Ic-Vc, are isomers of each other, and consequently, their preparation is similar, and in some respects identical. The synthetic schemes for both compound families are set forth in Schemes 1b/1c-6b/6c, below:

Schemes 1b and 1c

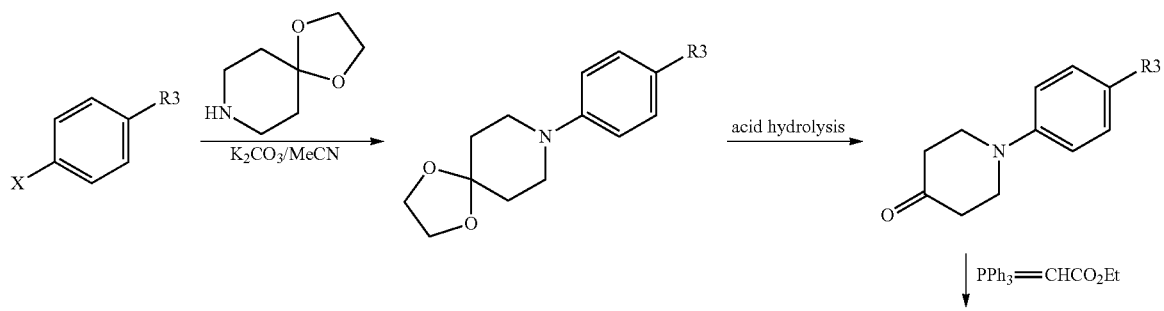

-continued

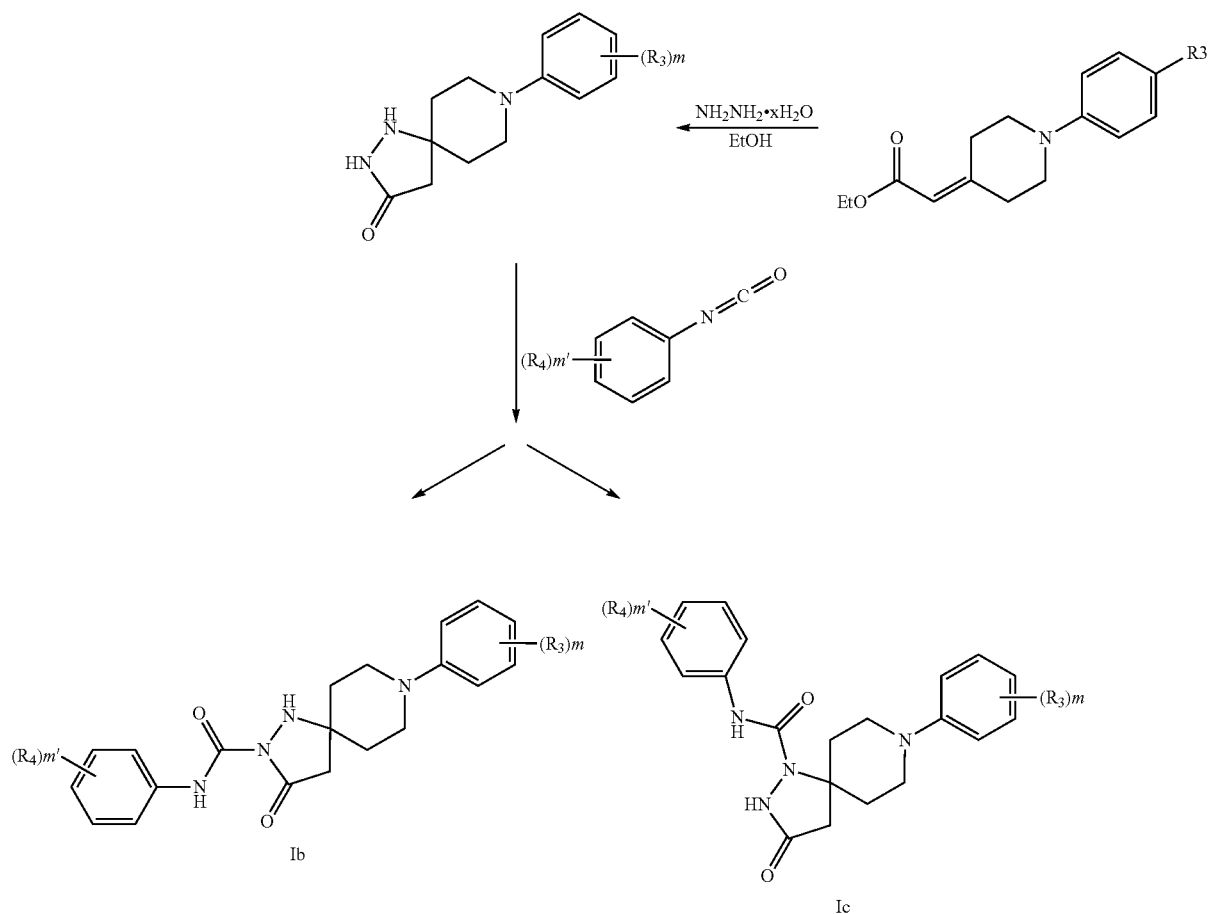

Representative Synthesis

Scheme 2b/2c

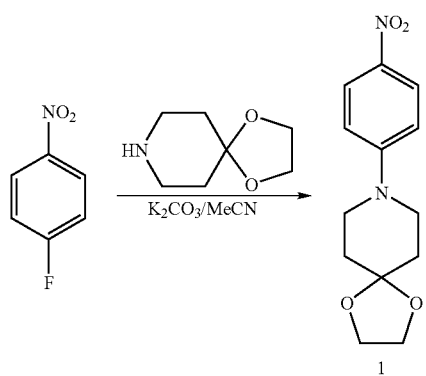

Scheme 3b/3c

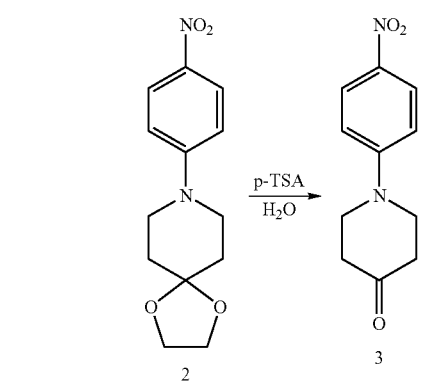

To 10 mL of acetonitrile (MeCN) was added K₂CO₃ (0.828 g, 6 mmol), 1,4-dioxa-8-azaspiro[4,5]decane (0.715 g, 5 mmol) and 1-fluoro-4-nitrobenzene (0.705 g, 5 mmol). The suspension was heated at reflux for 2 h under an argon atmosphere. MeCN was evaporated and the reaction mixture was diluted with H₂O (50 mL). The precipitated solid was collected by filteration and used as such for the next step.

The crude dioxalane derivative 1 was suspended in 150 mL of water and treated with 1 g of p-TSA. The mixture was refluxed for 4 h and then concentrated to 100 mL of volume. After cooling K₂CO₃ was added and the precipitated solid was collected by filteration, washed with water and dried to yield the piperidinone derivative 2 (840 mg).

Scheme 4b/4c

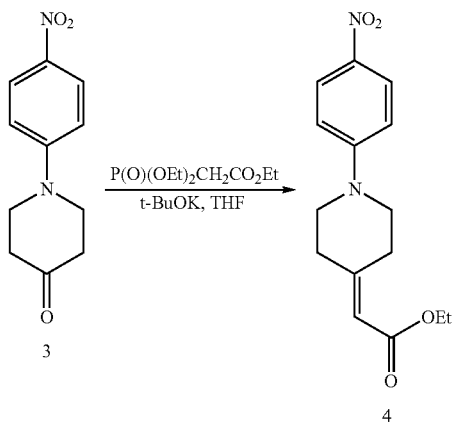

Potassium t-butoxide (760 mg, 6.8 mmol) was suspended in 20 ml of anhyd. THF. P(O)(OEt)$_2$CH$_2$CO$_2$Et (1.52 g, 6.8 mmol) was added and the mixture was stirred for 15 min. After adding the Ketone (3, 1.14 g, 5.2 mmol) the mixture was stirred for 20 min and then was poured into 200 ml of water. The precipitated solid was filtered, washed with water and dried. The intermediate ester was used as such for the next step without further purification.

Scheme 5b/5c

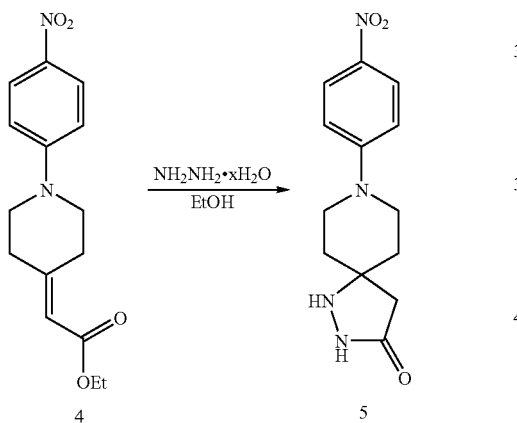

Scheme 6b/6c

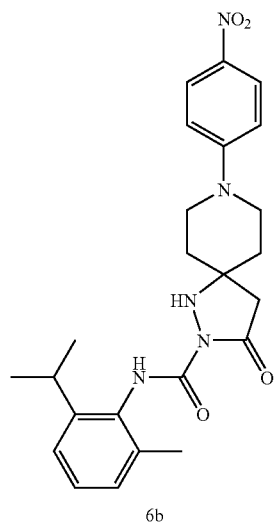

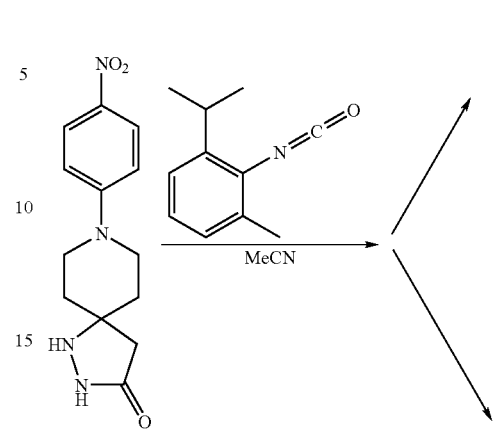

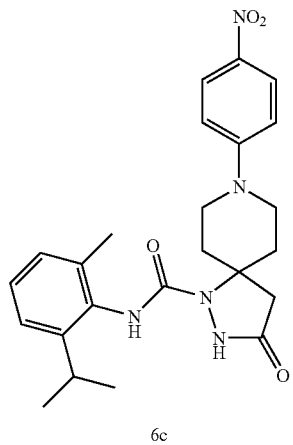

The cyclic hydrazide (5, 266 mg, 0.96 mmol) was suspended in dry acetonitrile (15 ml) and was treated with the phenylisocyanate derivative (240 mg, 1.37 mmol). The mixture was refluxed for 12 hr. The solvent was removed and the residue was purified using column chromatography on silica gel to afford the product 6. The product was then crystallized from hexane to yield the desired product (123 mg). The final product is separated by filtration and can be purified using various methods known to those skilled in the art.

Further, as can be seen from the foregoing schemes, compounds 6b and 6c are position isomers, that can form in corresponding amounts and yields from essentially the same synthetic protocol.

The exemplary compounds of the invention according to formulae 1a-Va, are prepared or can be prepared are shown in Table 1A, below.

TABLE 1A

| | Exemplary Compounds of Formulae 1a-5a | |
|---|---|---|
| ID | Structure | MW |
| 1a | | 395.42 |
| 2a | | 437.50 |
| 3a | | 451.53 |
| 4a | | 437.50 |
| 5a | | 437.50 |
| 6a | | 463.42 |

TABLE 1A-continued

Exemplary Compounds of Formulae 1a-5a

| ID | Structure | MW |
|---|---|---|
| 7a | 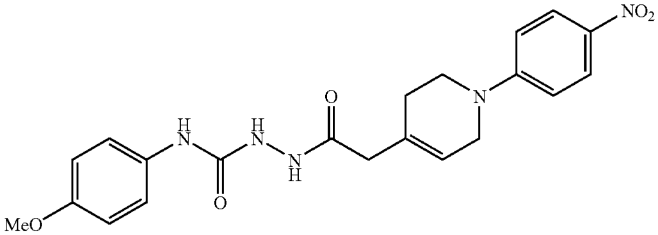 [SMILES: COc1ccc(NC(=O)NNC(=O)CC2=CCN(c3ccc([N+](=O)[O-])cc3)CC2)cc1] | 426.46 |
| 8a | 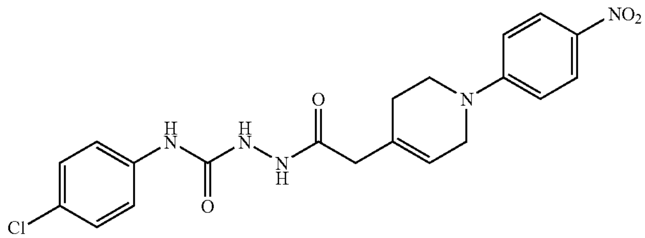 [SMILES: O=C(CC1=CCN(c2ccc([N+](=O)[O-])cc2)CC1)NNC(=O)Nc1ccc(Cl)cc1] | 429.87 |
| 9a | 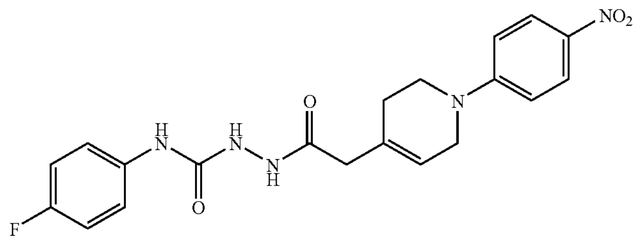 [SMILES: O=C(CC1=CCN(c2ccc([N+](=O)[O-])cc2)CC1)NNC(=O)Nc1ccc(F)cc1] | 413.41 |
| 10a | 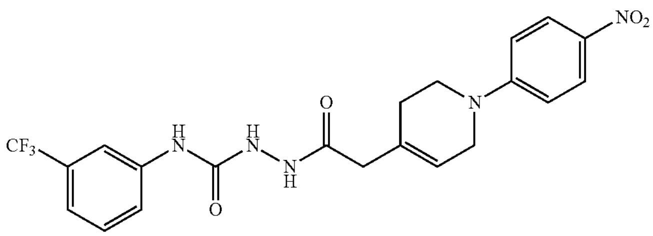 [SMILES: O=C(CC1=CCN(c2ccc([N+](=O)[O-])cc2)CC1)NNC(=O)Nc1cccc(C(F)(F)F)c1] | 463.42 |
| 11a | 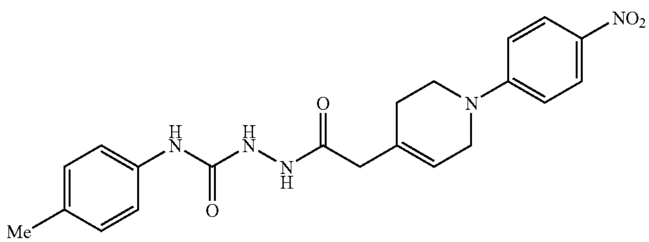 [SMILES: Cc1ccc(NC(=O)NNC(=O)CC2=CCN(c3ccc([N+](=O)[O-])cc3)CC2)cc1] | 409.45 |
| 12a | 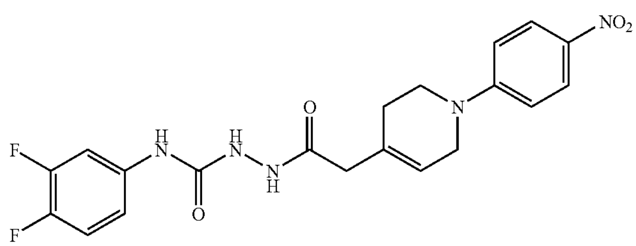 [SMILES: O=C(CC1=CCN(c2ccc([N+](=O)[O-])cc2)CC1)NNC(=O)Nc1ccc(F)c(F)c1] | 431.40 |

The exemplary compounds of the invention according to formulae 1b-Vb, are prepared or can be prepared are shown in Table 1B, below.

TABLE 1B

Exemplary Compounds of Formulae 1b-5b

| ID | Structure | MW |
|----|-----------|-----|
| 1b | 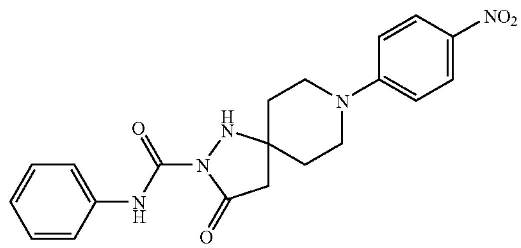 [SMILES: O=C1CC2(CCN(c3ccc([N+](=O)[O-])cc3)CC2)NN1C(=O)Nc1ccccc1] | 395.42 |
| 2b | 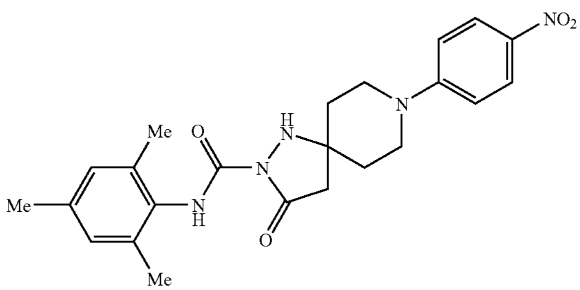 [SMILES: Cc1cc(C)c(NC(=O)N2NC3(CCN(c4ccc([N+](=O)[O-])cc4)CC3)CC2=O)c(C)c1] | 437.50 |
| 3b | 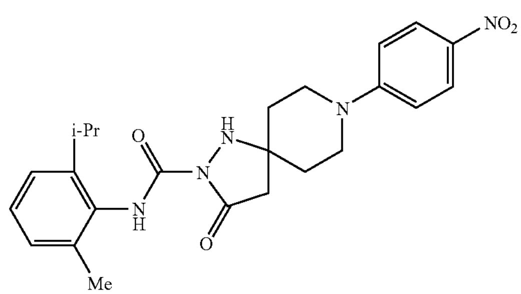 [SMILES: Cc1cccc(C(C)C)c1NC(=O)N1NC2(CCN(c3ccc([N+](=O)[O-])cc3)CC2)CC1=O] | 451.53 |
| 4b | 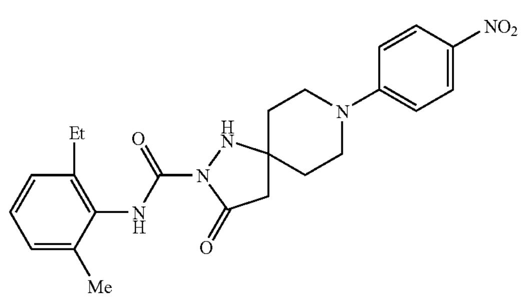 [SMILES: CCc1cccc(C)c1NC(=O)N1NC2(CCN(c3ccc([N+](=O)[O-])cc3)CC2)CC1=O] | 437.50 |
| 5b | 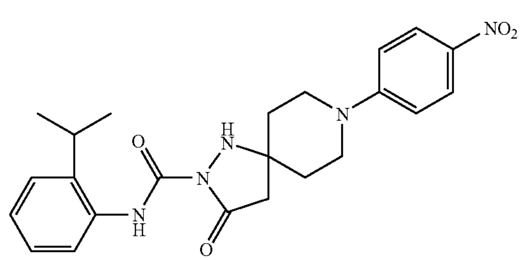 [SMILES: CC(C)c1ccccc1NC(=O)N1NC2(CCN(c3ccc([N+](=O)[O-])cc3)CC2)CC1=O] | 437.50 |

TABLE 1B-continued

Exemplary Compounds of Formulae 1b-5b

| ID | Structure | MW |
|---|---|---|
| 6b | (4-CF3-phenyl)-NH-C(O)-N(pyrazolidinone spiro piperidine)-N(4-NO2-phenyl) | 463.42 |
| 7b | (4-MeO-phenyl)-NH-C(O)-N(pyrazolidinone spiro piperidine)-N(4-NO2-phenyl) | 426.46 |
| 8b | (4-Cl-phenyl)-NH-C(O)-N(pyrazolidinone spiro piperidine)-N(4-NO2-phenyl) | 429.87 |
| 9b | (4-F-phenyl)-NH-C(O)-N(pyrazolidinone spiro piperidine)-N(4-NO2-phenyl) | 413.41 |
| 10b | (3-CF3-phenyl)-NH-C(O)-N(pyrazolidinone spiro piperidine)-N(4-NO2-phenyl) | 463.42 |
| 11b | (4-Me-phenyl)-NH-C(O)-N(pyrazolidinone spiro piperidine)-N(4-NO2-phenyl) | 409.45 |

TABLE 1B-continued

Exemplary Compounds of Formulae 1b-5b

| ID | Structure | MW |
|----|-----------|-----|
| 12b | 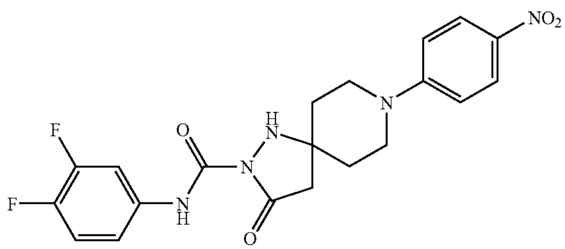 [SMILES: O=C1CC2(CCN(c3ccc([N+](=O)[O-])cc3)CC2)NN1C(=O)Nc1ccc(F)c(F)c1] | 431.40 |

The exemplary compounds of the invention according to formulae 1c-Vc, are prepared or can be prepared are shown in Table 1C, below.

TABLE 1C

Exemplary Compounds of Formulae 1c-5c

| ID | Structure | MW |
|----|-----------|-----|
| 1c | 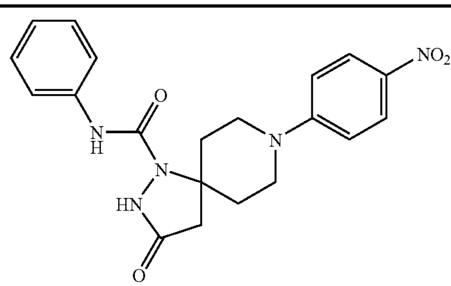 | 395.42 |
| 2c | 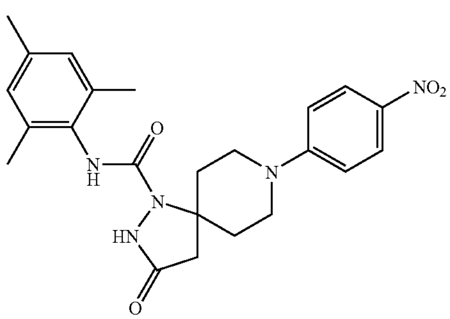 [SMILES: Cc1cc(C)c(NC(=O)N2NC(=O)CC23CCN(c2ccc([N+](=O)[O-])cc2)CC3)c(C)c1] | 437.50 |
| 3c | 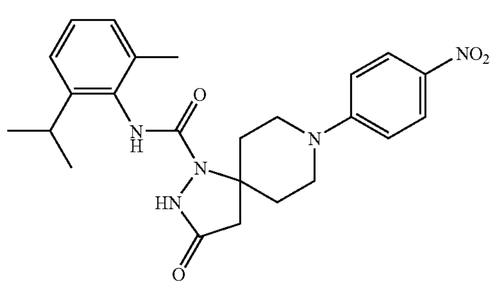 [SMILES: Cc1cccc(C(C)C)c1NC(=O)N1NC(=O)CC12CCN(c1ccc([N+](=O)[O-])cc1)CC2] | 451.53 |

TABLE 1C-continued

Exemplary Compounds of Formulae 1c-5c

| ID | Structure | MW |
|---|---|---|
| 4c | 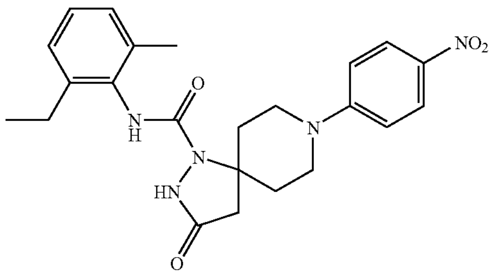 [SMILES: CCc1cccc(C)c1NC(=O)N1NC(=O)CC12CCN(c1ccc([N+](=O)[O-])cc1)CC2] | 437.50 |
| 5c | 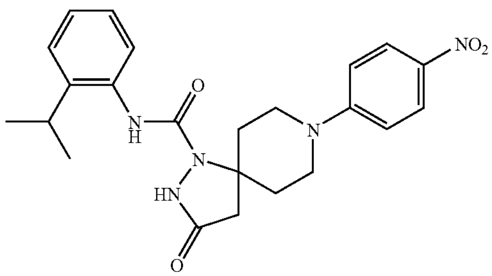 [SMILES: CC(C)c1ccccc1NC(=O)N1NC(=O)CC12CCN(c1ccc([N+](=O)[O-])cc1)CC2] | 437.50 |
| 6c | 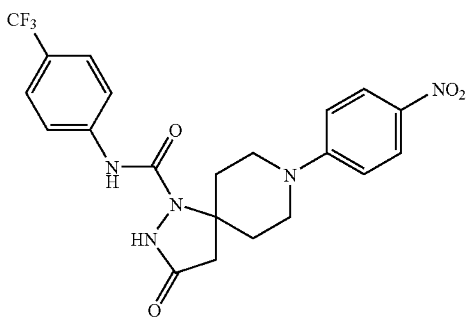 [SMILES: O=C1CC2(CCN(c3ccc([N+](=O)[O-])cc3)CC2)N(C(=O)Nc2ccc(C(F)(F)F)cc2)N1] | 463.42 |
| 7c | 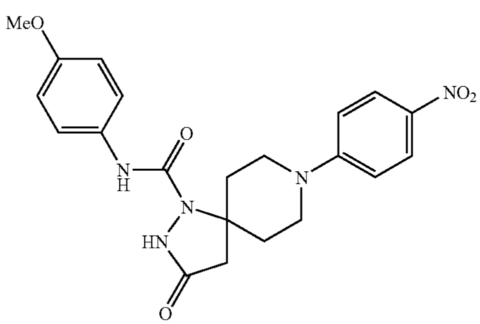 [SMILES: COc1ccc(NC(=O)N2NC(=O)CC23CCN(c2ccc([N+](=O)[O-])cc2)CC3)cc1] | 426.46 |
| 8c | 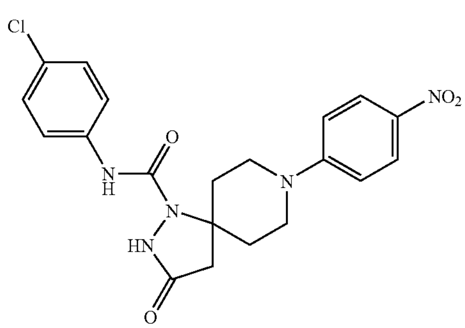 [SMILES: O=C1CC2(CCN(c3ccc([N+](=O)[O-])cc3)CC2)N(C(=O)Nc2ccc(Cl)cc2)N1] | 429.87 |

TABLE 1C-continued

Exemplary Compounds of Formulae 1c-5c

| ID | Structure | MW |
|----|-----------|-----|
| 9c | 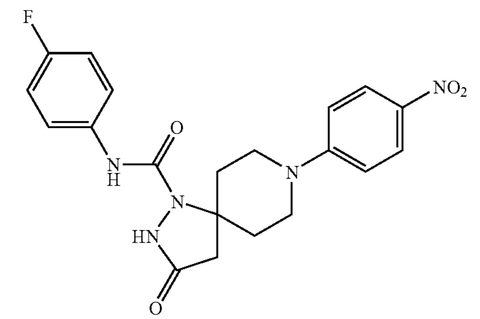 [SMILES: O=C1CC2(CCN(c3ccc([N+](=O)[O-])cc3)CC2)N(C(=O)Nc2ccc(F)cc2)N1] | 413.41 |
| 10c | 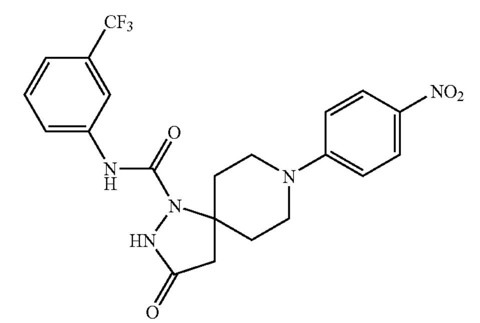 [SMILES: O=C1CC2(CCN(c3ccc([N+](=O)[O-])cc3)CC2)N(C(=O)Nc2cccc(C(F)(F)F)c2)N1] | 463.42 |
| 11c | 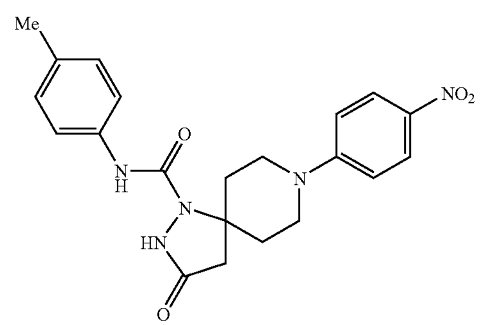 [SMILES: Cc1ccc(NC(=O)N2NC(=O)CC23CCN(c2ccc([N+](=O)[O-])cc2)CC3)cc1] | 409.45 |
| 12c | 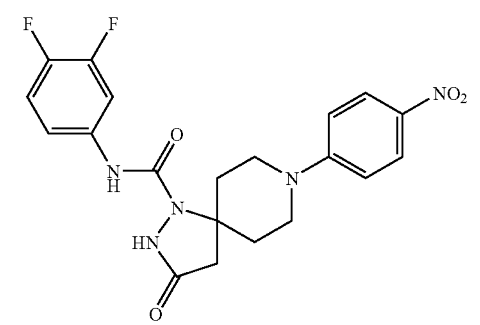 [SMILES: O=C1CC2(CCN(c3ccc([N+](=O)[O-])cc3)CC2)N(C(=O)Nc2ccc(F)c(F)c2)N1] | 431.40 |

Example 1

In order to study the inhibition of binding of $[^{125}I]T3$ to TRs in intact cells by the antagonist molecule Compounds of the invention, GH4 rat pituitary cells containing endogenous TRs (TRα1, TRβ1, and TRβ2) are grown in monolayer culture in DMEM medium containing 10% calf serum. Cells are dispersed by incubation in a buffered solution of EDTA and incubated at 37° C. for 60 min in serum-free DMEM to lower endogenous levels of thyroid hormones. Aliquots containing approximately 1.5 million cells are collected by centrifugation at 1000×g for 10 min and then suspended in 1 mL of serum free medium containing 0.1 nM $[^{125}I]T3$ and the indicated concentrations of unlabeled T3 or the antagonist candidate Compound. Following incubation at 37° C. for 60 min, the cells are chilled in ice and then centrifuged at 4° C. at 1000×g for 10 min. The samples are washed twice by re-suspension and vortexing with 1 ml of 50 mM Tris-HCl, pH 7.85, containing 1 mM $MgCl_2$ and 0.5% Triton X-100 and centrifugation at 1,000×g for 10 min to isolate the nuclear fraction of the cells. The amount of [$^{125}$I]T3 retained in the resulting pellet of washed nuclei is determined using a Packard gamma spectrometer.

Example 2

Functional CAT assays are performed to compare the extent of inhibition of the T3 stimulation of CAT activity observed in the presence of the antagonist candidates. HeLa cells are innoculated at 50,000 cells per well in 24 well plates in DMEM containing 10% calf serum. The cells are transfected 5 hours later by calcium phosphate precipitation using 450 ng of the T3 responsive ΔMTV-IR-CAT reporter and 250 ng of a vector expressing TRα. At the time of transfection, the cells also receive 6 nM T3 and the different concentrations of the antagonist candidates. Cells are harvested 40 h after transfection and assayed for protein content and CAT activity. Results are expressed as the extent of inhibition of the T3 stimulation of CAT activity observed in the presence of the antagonist candidates. Each data point reflects the average of triplicate samples which showed less than 10% variation. The assay results are set forth in FIG. 1.

Example 3

A study to compare the T3-mediated co-activator recruitment to TR by the compounds is conducted in vitro. Approximately 2.5-5×10$^4$ cpm of $^{35}$S-labeled TRα (20 fmol) in 2 μl of lysate is incubated with 500 ng of GST fused to the receptor interaction region of the co-activator NRC (NRC15) immobilized on a glutathione-agarose beads. The samples are also incubated for 15 min at room temperature with each of the compounds, in binding buffer. The samples are then chilled on ice and incubated with 1 nM T3 for an additional 60 min at 4° C. Control samples contain no T3 or antagonists, or receive only T3. The beads are washed and the bound $^{35}$S-TRα electrophoresed in a 10% SDS gel followed by analysis and quantitation of that amount of $^{35}$S-TRα bound using a Molecular Dynamics Phosphorimager and ImageQuant software. The percent inhibition of T3-mediated binding of $^{35}$S-TRα to GST-NRC15 by the compounds of the invention is determined after subtracting the amount of $^{35}$S-TRα bound to GST-NRC15 in the absence of T3.

The following references contain material associated with the field of the invention disclosed herein; however, no determination has been made with regard to the relevance or lack thereof of any of said references; moreover, no assertion that any of said references is or is not relevant to the invention is intended. In the event that any of said references is actually found to contain material relevant to the present invention, such reference should be considered incorporated in its entirety into this specification.

1. DeGroot Ed. (1995), Saunders Endocrinology, 3$^{rd}$ ed., L. J.
2. Werner and Ingbar (1996) The Thyroid: a Fundamental and Clinical Test, Lippincott-Raven, 7$^{th}$ ed., L. E. Braverman and R. D. Utiger, eds.
3. Wilson J. D. Ed. (1998), Saunders Williams Textbook of Endocrinology
4. Yen, P. M. (2001) Physiol. Rev. 81, 1097-1142.
5. Evans R M. (1988) The steroid and thyroid hormone receptor superfamily. Science 240:889-95
6. Carson-Jurica M A, Schrader W T, O'Malley B W. (1990) Steroid receptor family: structure and functions. Endocr Rev. 11:201-20.
7. Chambon P. (1993) The molecular and genetic dissection of the retinoid signaling pathway. Gene. 135:223-8.
8. Dees, E. C., Kennedy, M. J. (1998) Curr. Opin. Oncol. 10, 517-522.
9. Labrie F. (1993) Mechanism of action and pure antiandrogenic properties of flutamide. Cancer. 72:3816-27.
10. Olefsky J M, Saltiel A R (2000) PPAR gamma and the treatment of insulin resistance. Trends Endocrinol Metab. 11(9):362-8.
11. Forrest D, Erway L C, Ng L, Altschuler R, Curran T. (1996) Thyroid hormone receptor beta is essential for development of auditory function. Nat Genet. 13:354-7.
12. Weiss R E, Forrest D, Pohlenz J, Cua K, Curran T, Refetoff S. (1997) Thyrotropin regulation by thyroid hormone in thyroid hormone receptor beta-deficient mice. Endocrinology. 138:3624-9.
13. Wikstrom L, Johansson C, Salto C, Barlow C, Campos Barros A, Baas F, Forrest D, Thoren P, Vennstrom B. (1998) Abnormal heart rate and body temperature in mice lacking thyroid hormone receptor alpha 1. EMBO J. 17:455-61.
14. Brzozowski A M, Pike A C, Dauter Z, Hubbard R E, Bonn T, Engstrom O, Ohman L, Greene G L, Gustafsson J A, Carlquist M. (1997) Molecular basis of agonism and antagonism in the oestrogen receptor. Nature. 389:753-8.
15. Moras D, Gronemeyer H. (1998) The nuclear receptor ligand-binding domain: structure and function. Curr Opin Cell Biol., 10:384-91.
16. Weatherman R V, Fletterick R J, Scanlan T S. (1999) Nuclear-receptor ligands and ligand-binding domains. Annu Rev Biochem. 68:559-81.
17. Bourguet W, Germain P, Gronemeyer H. (2000) Nuclear receptor ligand-binding domains: three-dimensional structures, molecular interactions and pharmacological implications. Trends Pharmacol Sci. 21:381-8
18. Pike A C, Brzozowski A M, Walton J, Hubbard R E, Thorsell A G, Li Y L, Gustafsson J A, Carlquist M (2001) Structural insights into the mode of action of a pure anti-estrogen. Structure (Camb) 9:145-53.
19. Xu H E, Stanley T B, Montana V G, Lambert M H, Shearer B G, Cobb J E, McKee D D, Galardi C M, Plunket K D, Nolte R T, Parks D J, Moore J T, Kliewer S A, Willson T M, Stimmel J B. (2002) Structural basis for antagonist-mediated recruitment of nuclear co-repressors by PPARalpha. Nature. 415:813-7.
20. Shiau, A. K., Barstad, D., Radek, J. T. Meyers, M. J. Nettles, K. W., Katzellenbogen, B. S., Katzellenbogen, J. A., Agard, D. A., Greene, G. L. (2002) Nat. Struc. Biol. 9, 359-364.
21. Shiau, A. K., Barstad, D., Loria, P. M., Cheng, L., Kushner, P. J., Agard, D. A., Greene, G. L. (1998) The structural basis of estrogen receptor/coactivator recognition and the antagonism of this interaction by tamoxifen. Cell 95, 927-937.
22. Pike, A. C., Brzozowski, A. M., Hubbard, R. E., Bonn, T., Thorsell, A. G., Engstrom, O., Ljunggren, J., Gustafsson, J. A., Carlquist, M. (1999) EMBO J. 18, 4608-18.
23. Bourguet, W., Vivat, V., Wurtz, J. M., Chambon, P., Gronemeyer, H., Moras, D. (2000) Mol. Cell 5, 289-98.
24. Schapira M, Raaka B M, Samuels H H, Abagyan R. (2000) Rational discovery of novel nuclear hormone receptor antagonists Proc Natl Acad Sci USA. 97(3):1008-13.
25. Baxter J D, Goede P, Apriletti J W, West B L, Feng W, Mellstrom K, Fletterick R J, Wagner R L, Kushner P J, Ribeiro R C, Webb P, Scanlan T S, Nilsson S. (2002), Structure-based design and synthesis of a thyroid hormone receptor (TR) antagonist. Endocrinology; 143(2):517-24.
26. Darimont, B. D., Wagner, R. L., Apriletti, J. W., Stallcup, M. R., Kushner, P. J., Baxter, J. D., Fletterick, R. J., Yamamoto, K. R. (1998) Genes Dev. 12, 3343-56.

27. Molsoft L L C, ICM 2.8 manual, freely available online at www.molsoft.com (Molsoft, San Diego, Calif.).
28. Abagyan, R., Totrov, M. (1994) J. Mol. Biol. 235, 983-1002.
29. Totrov, M., Abagyan, R. (1997) Proteins, Suppl. 1, 215-20.
30. Totrov, M., Abagyan, R., (2001) in Drug-Receptor Thermodynamics: Introduction and Applications, ed., Raffa, R. B. (J. Wiley & Sons, Ltd.), pp. 603-624.
31. Abagyan, R., Totrov, M. (2001) Curr. Opin. Chem. Biol. 5, 375-82.
32. Raaka, B. M., Samuels, H. H. (1983) J. Biol. Chem. 258, 417-425.
33. Mahajan M A and Samuels R H. (2000). A new family of nuclear receptor coregulators that integrate nuclear receptor signaling through CREB-binding protein. Mol. Cell. Biol. 20; 5048-5063.
34. Li, D., Desai-Yajnik, V., Lo, E., Schapira, M., Abagyan, R., Samuels, H. H. (1999) Mol. Cell. Biol. 19, 7191-202.
35. Lipinski C A, Lombardo F, Dominy B W, Feeney P J. (2001) Experimental and computational approaches to estimate solubility and permeability in drug discovery and development settings. Adv Drug Deliv Rev.; 46(1-3):3-26.
36. Bourguet W., Ruff M., Chambon P., Gronemeyer H., Moras D. (1995) Nature 375, 377-82.
37. Strynadka N. C., Eisenstein M., Katchalski-Katzir E., Shoichet B. K., Kuntz I. D., Abagyan R., Totrov M., Janin J., Cherfils J., Zimmerman F., Olson A., Duncan B., Rao M., Jackson R., Sternberg M., James M. N. (1996) Nat Struct Biol. 3, 233-9.
38. Abagyan R., Batalov S., Cardozo T., Totrov M., Webber J., Zhou Y. (1997) Proteins., Suppl 1, 29-37.
39. Ajay A, Walters W P, Murcko M A. (1998) Can we learn to distinguish between "drug-like" and "nondrug-like" molecules? J Med Chem.; 41(18):3314-24.
40. Barratt M D, Rodford R A. (2001) The computational prediction of toxicity. Curr Opin Chem Biol. 5(4):383-8.
41. Casanova J, Horowitz Z D, Copp R P, McIntyre W R, Pascual A, Samuels H H. (1984) Photoaffinity labeling of thyroid hormone nuclear receptors. Influence of n-butyrate and analysis of the half-lives of the 57,000 and 47,000 molecular weight receptor forms J Biol Chem.; 259(19):12084-91
42. Egea P F, Mitschler A, Rochel N, Ruff M, Chambon P, Moras D. (2000) Crystal structure of the human RXRalpha ligand-binding domain bound to its natural ligand: 9-cis retinoic acid. EMBO J. June 1; 19(11):2592-601.
43. Filikov A V, Mohan V, Vickers T A, Griffey R H, Cook P D, Abagyan R A, James T L. (2000) Identification of ligands for RNA targets via structure-based virtual screening: HIV-1 TAR J Comput Aided Mol Des. 14(6):593-610.
44. Greene N. (2002) Computer systems for the prediction of toxicity: an update. Adv Drug Deliv Rev.; 54(3):417-31
45. Lazar M A (1993) Thyroid hormone receptors: multiple forms, multiple possibilities. Endocr Rev. 14 (2):184-93
46. Macchia P E, Takeuchi Y, Kawai T, Cua K, Gauthier K, Chassande O, Seo H, Hayashi Y, Samarut J, Murata Y, Weiss R E, Refetoff S. (2001) Increased sensitivity to thyroid hormone in mice with complete deficiency of thyroid hormone receptor alpha. Proc Natl Acad Sci USA; 98(1): 349-54.
47. McGovern S L, Caselli E, Grigorieff N, Shoichet B K. (2002) A common mechanism underlying promiscuous inhibitors from virtual and high-throughput screening. J Med Chem. 45(8):1712-22.
48. Nolte R T, Wisely G B, Westin S, Cobb J E, Lambert M H, Kurokawa R, Rosenfeld M G, Willson T M, Glass C K, Milburn M V. (1998) Ligand binding and co-activator assembly of the peroxisome proliferator-activated receptor-gamma. Nature 395(6698):137-43.
49. Onate S A, Tsai S Y, Tsai M-J, and O'Malley B W. (1995) Sequence and characterization of a coactivator of the steroid hormone receptor superfamily. Science 270; 1354-1357.
50. Oppenheimer J H, Koerner D, Schwartz H L, Surks M I (1972) J. clin. Endocrinol. Metab. 35:330-33
51. Oppenheimer, J. H. and H. H. Samuels. 1983. Molecular Basis of Thyroid Hormone Action. Academic Press, New York
52. Pohlenz J, Maqueem A, Cua K, Weiss R E, Van Sande J, Refetoff S. (1999) Improved radioimmunoassay for measurement of mouse, thyrotropin in serum: strain differences in thyrotropin concentration and thyrotroph sensitivity to thyroid hormone. Thyroid.; 9(12):1265-71.
53. Powers C A, Mathur M, Raaka B M, Ron D, and Samuels H H. (1998) TLS (Translocated-in-Liposarcoma) is a high-affinity interactor for steroid, thyroid hormone, and retinoid receptors. Mol. Endocrinol. 12; 4-18.
54. Refetoff S. (1997) Resistance to thyroid hormone. Curr Ther Endocrinol Metab.; 6:132-4.
55. Sadowski J, Kubinyi H. (1998) A scoring scheme for discriminating between drugs and nondrugs. J Med Chem. 41(18):3325-9.
56. Samuels H H, Tsai J S. (1973) Thyroid hormone action in cell culture: demonstration of nuclear receptors in intact cells and isolated nuclei. Proc Natl Acad Sci USA. 70:3488-92
57. Schapira M, Raaka B M, Samuels H H, Abagyan R. (2001) In silico discovery of novel Retinoic Acid Receptor agonist structures. BMC Struct Biol. 2001; 1(1):1.
58. Steinmetz A C, Renaud J P, Moras D. (2001) Binding of ligands and activation of transcription by nuclear receptors. Annu Rev Biophys Biomol Struct. 30:329-59.
59. Takeuchi Y, Murata Y, Sadow P, Hayashi Y, Seo H, Xu J, O'Malley B W, Weiss R E, and Refetoff S. (2002) Steroid receptor coactivator-1 deficiency causes variable alterations in the modulation of T(3)-regulated transcription of genes in vivo. Endocrinology 143; 1346-52.
60. Veber D F, Johnson S R, Cheng H Y, Smith B R, Ward K W, Kopple K D. (2002) Molecular properties that influence the oral bioavailability of drug candidates J. Med. Chem., 45 (12), 2615-2623.
61. Viswanadhan V N, Balan C, Hulme C, Cheetham J C, Sun Y. (2002) Knowledge-based approaches in the design and selection of compound libraries for drug discovery. Curr Opin Drug Discov Devel.; 5(3):400-6.
62. Wagner, R. L., Darimont, B. D., Apriletti, J. W., Stallcup, M. R., Kushner, P. J., Baxter, J. D., Fletterick, R. J., Yamamoto, K. R. (1998) Structure and Specificity of Nuclear Receptor: Coactivator Interactions Genes Dev. 12, 3343.
63. Walters W P, Ajay, Murcko M A. (1999) Recognizing molecules with drug-like properties. Curr Opin Chem Biol. August; 3(4):384-7.
64. Weiss R E, Refetoff S. (2000) Resistance to thyroid hormone. Rev Endocr Metab Disord. 1(1-2):97-108
65. Weiss R E, Chassande O, Koo E K, Macchia P E, Cua K, Samarut J, Refetoff S, Refetoff S. (2002) Thyroid function and effect of aging in combined hetero/homozygous mice deficient in thyroid hormone receptors alpha and beta genes. J Endocrinol.; 172(1):177-85.
66. Weiss R E, Xu J, Ning G, Pohlenz J, O'Malley B W, and Refetoff S. (1999). Mice deficient in the steroid receptor co-activator 1 (SRC-1) are resistant to thyroid hormone. Embo J. 18; 1900-4.

67. Taylor, E. C.; Skotnicki, J. S. Synthesis. (1981), 8, 606.
68. Hu, Y.; Zorumski, C. F.; Covey, D. F. J. Org. Chem. (1995), 60, 3619.
69. Wang G.; Hollingsworth, R. I. Tetrahedron: Asymmetry (1999), 10, 1895.
70. Plenat F.; Cassagne, M.; Cristau, H. J. Tetrahedron. (1995), 35, 9551

All publications, patents and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. All such modifications coming within the scope of the appended claims are intended to be included therein.

In general, the nomenclature used in this application is based on AUTONOM™ v.4.0, a Beilstein Institute computerized system for the generation of IUPAC systematic nomenclature. Chemical structures shown herein were prepared using ISIS®/DRAW version 2.5. Any open valency appearing on a carbon, oxygen or nitrogen atom in the structures herein indicates the presence of a hydrogen atom. Where a chiral center exists in a structure but no specific stereochemistry is shown for the chiral center, both enantiomers associated with the chiral structure are encompassed by the structure.

Any chemical names of compounds given in this application were generated using Open Eye Software's Lexichem naming tool, Symyx Renaissance Software's Reaction Planner or MDL's ISIS Draw Autonom Software tool, and are not verified. Preferably, in the event of inconsistency, the depicted structure governs.

What is claimed is:

1. A compound of formula Ia:

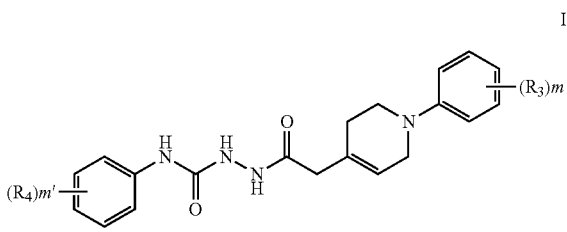

Ia or a pharmaceutically acceptable salt thereof, and stereoisomers, tautomers and thereof; and
wherein:
each of $R^3$ and $R^4$ are independently H, substituted or unsubstituted alkyl, substituted or unsubstituted alkoxy, substituted or unsubstituted amino, substituted or unsubstituted amido, $NHSO_2$-alkyl, halo, or nitro; and
each of m and m' are independently selected from 0-4.

2. The compound of claim 1 wherein $R^3$ is alkyl, nitro, alkoxy, halo or haloalkyl.

3. The compound of claim 1 wherein $R^4$ is alkyl, alkoxy, halo or haloalkyl and m' is 1.

4. The compound of claim 1 wherein each $R^4$ is independently alkyl, alkoxy, halo or haloalkyl and m' is 2.

5. The compound of claim 1 wherein the compound is according to formula IIa:

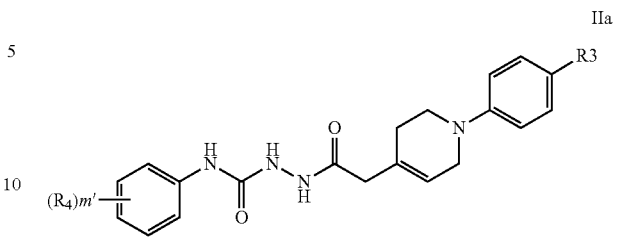

IIa or a pharmaceutically acceptable salt thereof, and stereoisomers, tautomers and isotopic variants thereof; and
wherein:
each of $R^3$ and $R^4$ are independently H, substituted or unsubstituted alkyl, substituted or unsubstituted alkoxy, substituted or unsubstituted amino, substituted or unsubstituted amido, $NHSO_2$-alkyl, halo, or nitro; and
m' is selected from 0-4.

6. The compound of claim 5 wherein $R^3$ is alkyl, nitro, alkoxy, halo or haloalkyl.

7. The compound of claim 5 wherein $R^4$ is alkyl, alkoxy, halo or haloalkyl and m' is 1.

8. The compound of claim 5 wherein each $R^4$ is independently alkyl, alkoxy, halo or haloalkyl and m' is 2.

9. The compound of claim 1 wherein the compound is of formula III

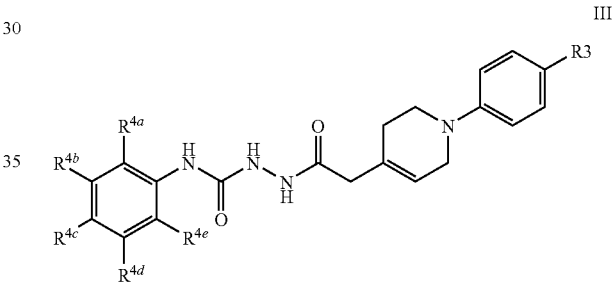

III or a pharmaceutically acceptable salt thereof, and stereoisomers, tautomers and isotopic variants thereof; and
wherein:
each of $R^3$ and $R^{4a-e}$ are independently H, substituted or unsubstituted alkyl, substituted or unsubstituted alkoxy, substituted or unsubstituted amino, substituted or unsubstituted amido, $NHSO_2$-alkyl, halo, or nitro.

10. The compound of claim 9 wherein $R^3$ is alkyl, nitro, alkoxy, halo or haloalkyl.

11. The compound of claim 1 wherein the compound is according to formula IVa:

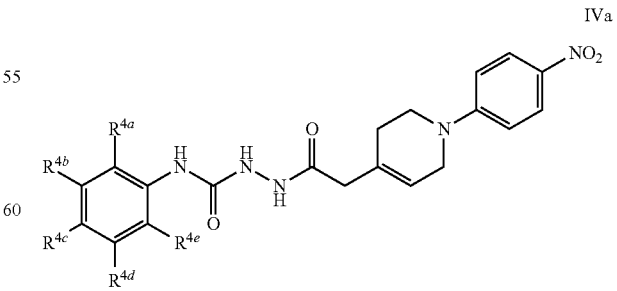

IVa or a pharmaceutically acceptable salt thereof, and stereoisomers, tautomers and isotopic variants thereof; and
wherein:

each of R⁴ᵃ⁻ᵉ are independently H, substituted or unsubstituted alkyl, substituted or unsubstituted alkoxy, substituted or unsubstituted amino, substituted or unsubstituted amido, NHSO₂-alkyl, halo, or nitro.

12. The compound of claim 1 wherein the compound is of formula V

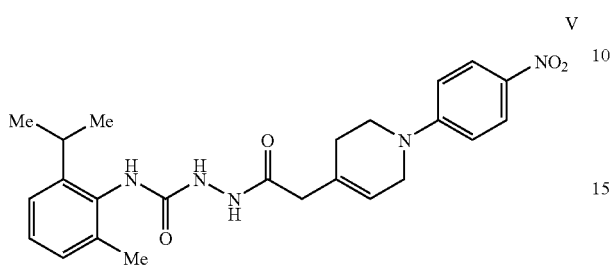

or a pharmaceutically acceptable salt thereof, and stereoisomers, tautomers and thereof.

13. A pharmaceutical composition comprising a pharmaceutically acceptable carrier and a pharmaceutically effective amount of a compound of claim 1.

14. The pharmaceutical composition of claim 13 wherein the carrier is a parenteral carrier, oral or topical carrier.

15. The compound of claim 1, wherein each R³ is independently H, NO₂, CF₃, F, Cl, or NHSO₂Me.

16. The compound of claim 1, wherein each R⁴ is independently H, Me, Et, iso-Pr, CF₃, OMe, F, or Cl.

17. The compound of claim 1, wherein the compound is selected from

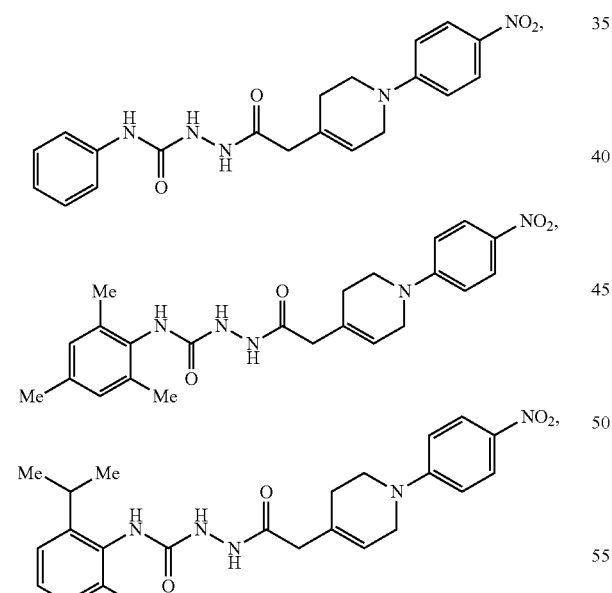

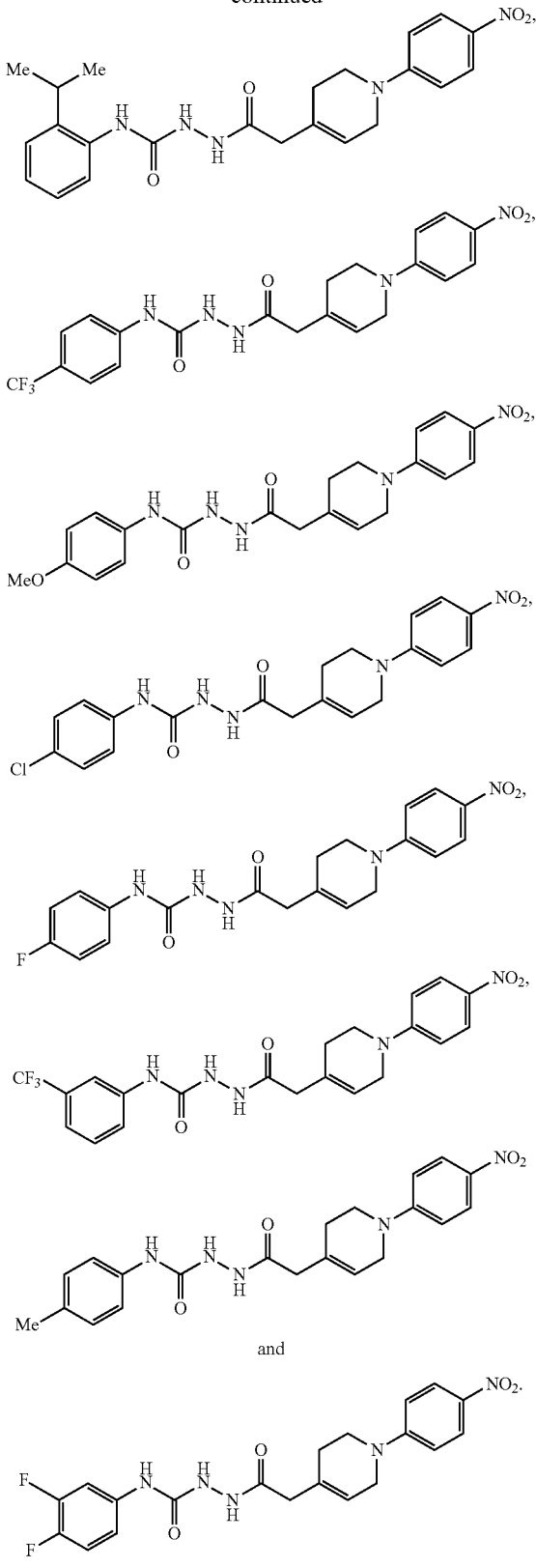

* * * * *